United States Patent
Pérez Encabo et al.

(10) Patent No.: US 10,597,386 B2
(45) Date of Patent: Mar. 24, 2020

(54) PROCESS AND INTERMEDIATES FOR THE PREPARATION OF BENZO[B]THIOPHENE COMPOUNDS

(71) Applicant: CRYSTAL PHARMA, S.A.U., Boecillo, Valladolid (ES)

(72) Inventors: Alfonso Pérez Encabo, Valladolid (ES); José Ángel Turiel Hernandez, Valladolid (ES); Yolanda Fernández Sainz, Valladolid (ES); Antonio Lorente Bonde-Larsen, Valladolid (ES)

(73) Assignee: Crystal Pharma, S.A.U., Boecillo, Valladolid (ES)

( * ) Notice: Subject to any disclaimer, the term of this patent is extended or adjusted under 35 U.S.C. 154(b) by 0 days.

(21) Appl. No.: 15/764,616

(22) PCT Filed: Sep. 30, 2016

(86) PCT No.: PCT/EP2016/073414
§ 371 (c)(1),
(2) Date: Mar. 29, 2018

(87) PCT Pub. No.: WO2017/055543
PCT Pub. Date: Apr. 6, 2017

(65) Prior Publication Data
US 2019/0040048 A1    Feb. 7, 2019

(30) Foreign Application Priority Data

Oct. 2, 2015    (EP) .................................. 15382479

(51) Int. Cl.
*C07D 409/04*    (2006.01)
*C07D 215/227*    (2006.01)
(Continued)

(52) U.S. Cl.
CPC ....... *C07D 409/04* (2013.01); *C07D 215/227* (2013.01); *C07D 241/12* (2013.01);
(Continued)

(58) Field of Classification Search
CPC ............ C07D 215/227; C07D 295/033; C07D 295/15; C07D 417/14; C07D 409/12; C07D 401/12; C07D 241/12; C07D 409/04
See application file for complete search history.

(56) References Cited

U.S. PATENT DOCUMENTS 5,436,246 A    7/1995 Bernotas
2016/0272624 A1    9/2016 Liu et al.

FOREIGN PATENT DOCUMENTS

WO    05121087    12/2005
WO    WO 2005/121087 A1    12/2005
(Continued)

OTHER PUBLICATIONS

Ruhland T et al., "Iron-Assisted Nucleophilic Aromatic Substitution on Solid Phase", The Journal of Organic Chemistry, American Chemical Society, vol. 67, No. 15, Jan. 2002, pp. 5257-5268.

*Primary Examiner* — Alexander R Pagano
*Assistant Examiner* — Ebenezer O Sackey
(74) *Attorney, Agent, or Firm* — Gary J. Gershik; Cooper & Dunham LLP

(57) ABSTRACT

A process for preparing compounds of formula (I), or a salt or solvate thereof, including Brexpiprazole, which process comprises cyclization of a compound of formula (II) or (III), or a salt or solvate thereof. The invention also refers to intermediates of said process.

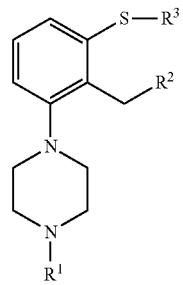

(II)

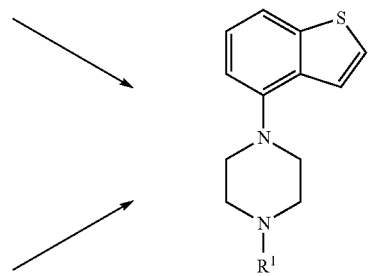

(I)

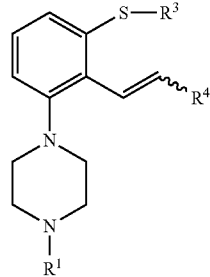

(III)

14 Claims, No Drawings

(51) Int. Cl.
*C07D 295/15* (2006.01)
*C07D 295/033* (2006.01)
*C07D 409/12* (2006.01)
*C07D 401/12* (2006.01)
*C07D 241/12* (2006.01)
*C07D 417/14* (2006.01)

(52) U.S. Cl.
CPC ....... *C07D 295/033* (2013.01); *C07D 295/15* (2013.01); *C07D 401/12* (2013.01); *C07D 409/12* (2013.01); *C07D 417/14* (2013.01)

(56) References Cited

FOREIGN PATENT DOCUMENTS

| WO | WO 2006/112464 A1 | | 10/2006 |
|----|-------------------|---|---------|
| WO | 13015456 | | 1/2013 |
| WO | 2013015456 | * | 1/2013 |
| WO | WO 2013/015456 A1 | | 1/2013 |
| WO | WO 2015/054976 A1 | | 4/2015 |

* cited by examiner

PROCESS AND INTERMEDIATES FOR THE PREPARATION OF BENZO[B]THIOPHENE COMPOUNDS

RELATED APPLICATIONS

This application is a § 371 national stage of PCT International Application No. PCT/EP2016/073414, filed Sep. 30, 2016, claiming priority of European Patent Application No. EP 15 382 479.2, filed Oct. 2, 2015, the contents of each of which are hereby incorporated by reference into this application.

FIELD OF THE INVENTION

The invention relates to a process for preparing benzo[b]thiophene compounds that can be used to obtain therapeutically useful compounds, such as Brexpiprazole.

BACKGROUND OF THE INVENTION

Brexpiprazole, discovered by Otsuka, is a dopamine D2 receptor partial agonist. It has been recently approved by the FDA for the treatment of schizophrenia and as an adjunctive therapy for the treatment of major depression.

The chemical name of Brexpiprazole is (7-{4-[4-(1-benzothiophen-4-yl)piperazin-1-yl]butoxy}quinolin-2(1H)-one), and is represented by the following formula:

The synthesis of this compound was first disclosed in EP 1869025 by a process comprising palladium-catalyzed cross-coupling of non-commercial 4-bromo-benzo[b]thiophene and piperazine, followed by substitution of the piperazine with the butoxy-quinolinone derivative (Reference Example 30 and Example 1).

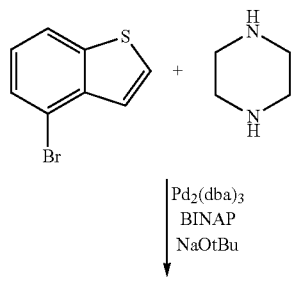

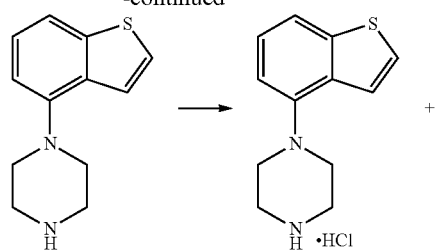

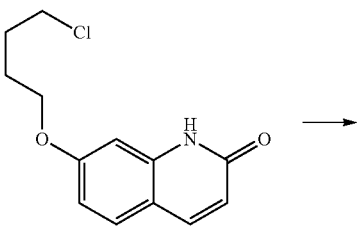

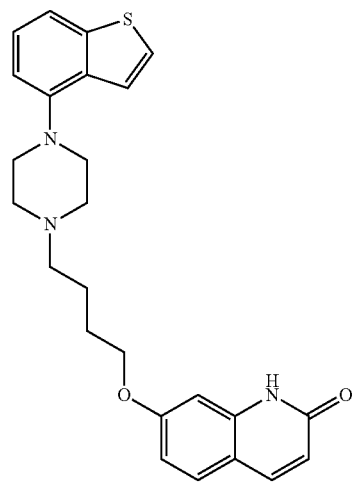

In addition to being expensive, the Pd-catalyzed cross-coupling reaction is not clean and gives rise to a product with reduced purity, as acknowledged by the applicant in the subsequent patent application WO 2013/015456.

WO 2013/015456 discloses a similar method for preparing Brexpiprazole, but starting from 4-chloro-benzo[b]thiophene and using smaller amounts of Pd and phosphines to cheapen the process (Examples 1-4). However, obtaining 4-chloro-benzo[b]thiophene requires a complex synthesis including a decarboxylation step that is performed under very high temperatures (145-195° C.). These reaction conditions are difficult to conduct at an industrial scale and, in our experience, this method does not proceed cleanly.

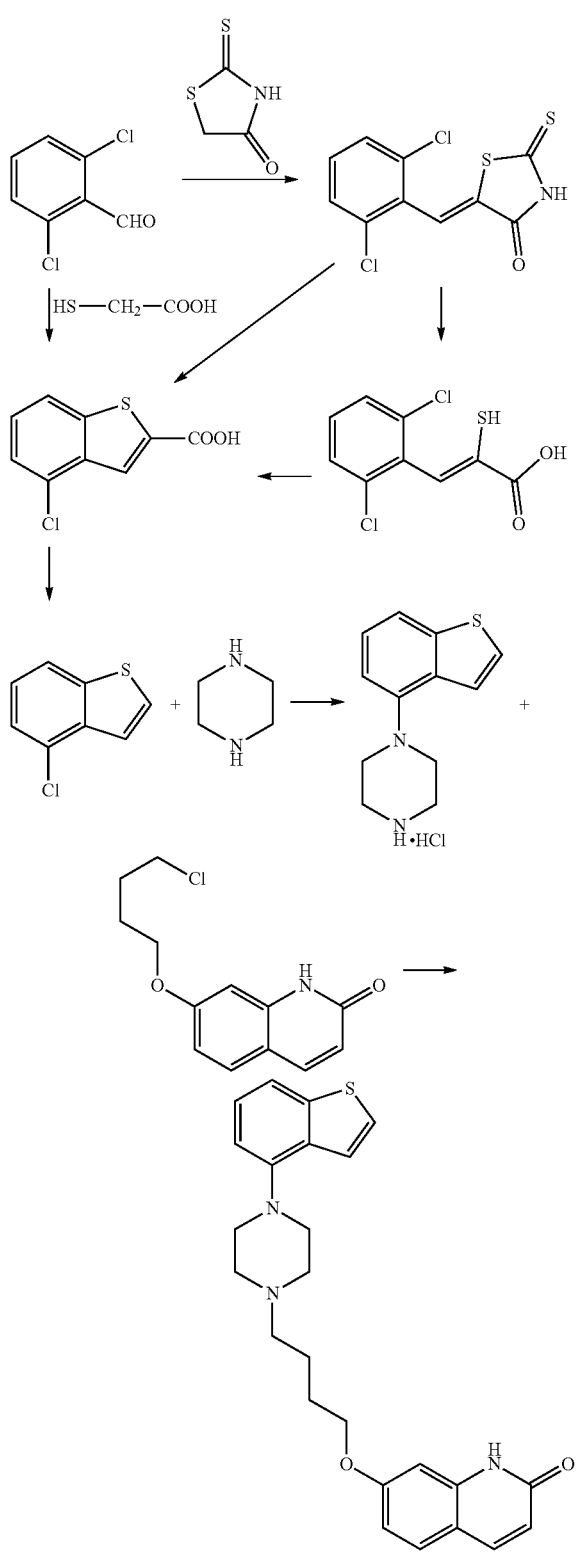

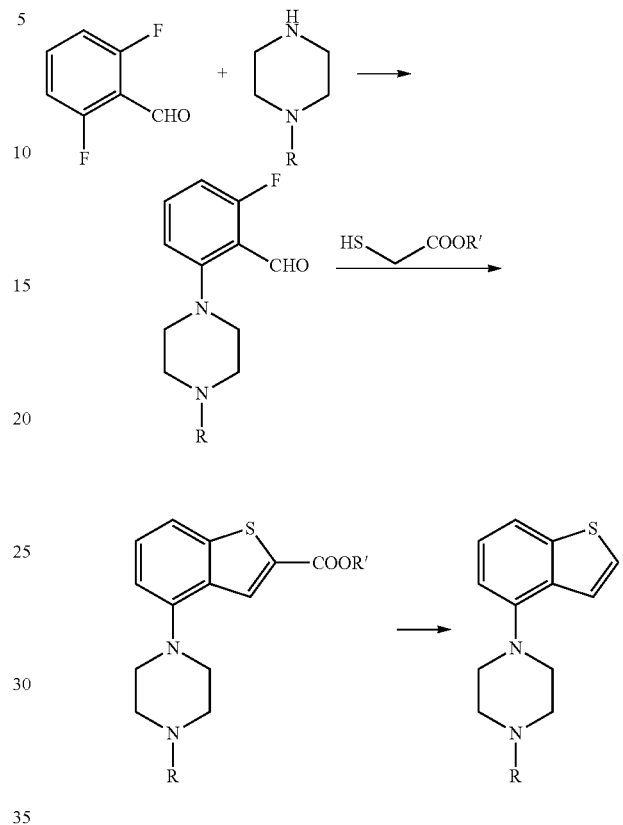

Other approaches for the synthesis of 4-piperazino-benzo[b]thiophene derivatives are disclosed in U.S. Pat. No. 5,436,246 and WO 2015/054976, where the use of organometallic compounds is avoided by introducing the piperazine derivative in a dihalobenzaldehyde at the beginning of the synthesis and then performing a cyclization reaction to obtain the benzo[b]thiophene ring. However, a final decarboxylation reaction is also needed to obtain Brexpiprazole.

In summary, the processes disclosed for the synthesis of 4-piperazino-benzo[b]thiophene derivatives require the use of organometallic reagents and/or a decarboxylation step at very high temperatures, which is an industrial limitation and does not favour clean and efficient processes.

As a consequence, it is still necessary to develop a process for the preparation of Brexpiprazole and related compounds that overcomes all or part of the problems associated with the known processes belonging to the state of the art.

SUMMARY OF THE INVENTION

The invention faces the problem of providing an improved process for the synthesis of piperazine substituted benzo[b]thiophene compounds, such as Brexpiprazole. The inventors have found that compounds of formula (II) and (III) can be efficiently used as intermediates in the synthesis of piperazine substituted benzo[b]thiophene compounds. Therefore, the invention refers to the use of compounds of formula (II) or (III), or salts or solvates thereof, as intermediates in the synthesis of compounds of formula (I), or salts or solvates thereof, such as Brexpiprazole.

Compounds of formula (I) can be readily obtained by cyclization of compounds of formula (II) or (III). Using this strategy, decarboxylation reactions on the benzo[b]thiophene compound can be avoided. Additionally, the synthetic method of the invention is suitable for the industrial process and allows a straightforward, efficient and clean synthesis of piperazine substituted benzo[b]thiophene compounds.

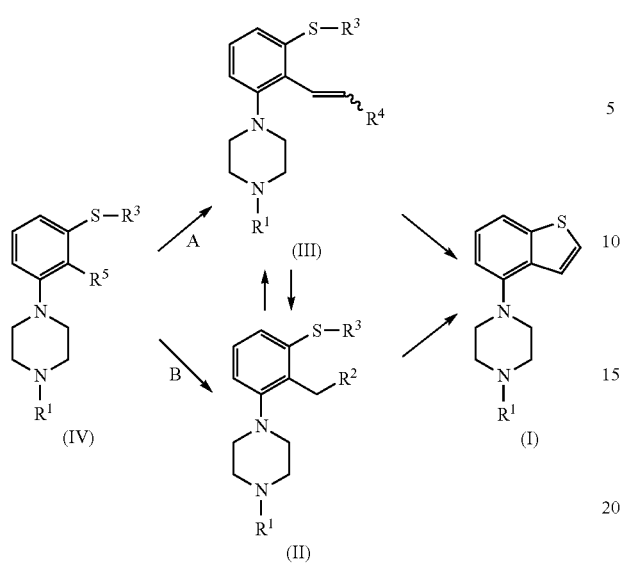

(IV) → (III) ⇌ (II) → (I)

Compounds of formula (II) and (III) can be interconverted. For instance, as disclosed herein, a compound of formula (III), or a salt or solvate thereof, can be converted into a compound of formula (II), or a salt or solvate thereof, through a process comprising a hydrolysis reaction. In turn, both compounds of formula (II) and compounds of formula (III), or a salt or solvate thereof, can be obtained from compounds of formula (IV), or a salt or solvate thereof.

Accordingly, in a first aspect the invention is directed to a process for preparing a compound of formula (I), or a salt or solvate thereof

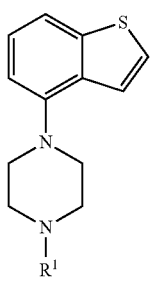

(I)

wherein $R^1$ is selected from hydrogen, an amino protecting group, —(CH$_2$)$_n$—X, —(CH$_2$)$_n$—OR,

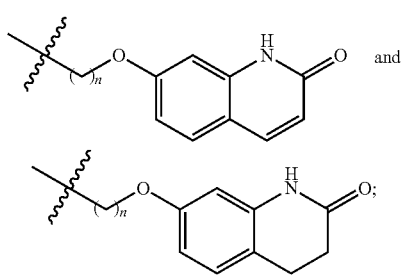

and n is an integer from 1 to 6;

X is a leaving group;

R is selected from H and a hydroxyl protecting group; which process comprises cyclization of a compound of formula (II), or a salt or solvate thereof

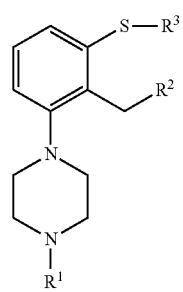

(II)

wherein $R^1$ is as defined above;

$R^2$ is selected from —CHO, —CN, —C(O)OR and —C(O)X';

X' is halogen;

R' is selected from H, $C_1$-$C_6$ alkyl, $C_6$-$C_{10}$ aryl and ($C_6$-$C_{10}$)aryl($C_1$-$C_6$)alkyl;

$R^3$ is selected from $C_1$-$C_6$ alkyl, $C_6$-$C_{10}$ aryl, ($C_6$-$C_{10}$)aryl ($C_1$-$C_6$)alkyl, —C(O)OR", —C(S)OR" and —C(O)R"; and R" is selected from $C_1$-$C_6$ alkyl, $C_6$-$C_{10}$ aryl and ($C_6$-$C_{10}$) aryl($C_1$-$C_6$)alkyl.

In a second aspect, the invention is directed to a process for preparing a compound of formula (I), or a salt or solvate thereof, as defined above, which process comprises cyclization of a compound of formula (III), or a salt or solvate thereof

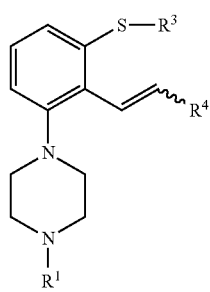

(III)

wherein $R^1$ is as defined above;

$R^4$ is selected from halogen and —OR';

R' is selected from $C_1$-$C_6$ alkyl, $C_6$-$C_{10}$ aryl and ($C_6$-$C_{10}$) aryl($C_1$-$C_6$)alkyl;

$R^3$ is selected from $C_1$-$C_6$ alkyl, $C_6$-$C_{10}$ aryl, ($C_6$-$C_{10}$)aryl ($C_1$-$C_6$)alkyl, —C(O)OR", —C(S)OR" and —C(O)R"; and R" is selected from $C_1$-$C_6$ alkyl, $C_6$-$C_{10}$ aryl and ($C_6$-$C_{10}$) aryl($C_1$-$C_6$)alkyl.

In another aspect, the invention is directed to a compound of formula (II), or a salt o solvate thereof

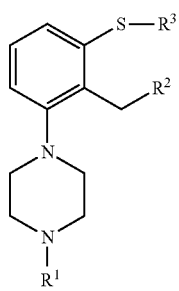

(II)

wherein

R¹ is selected from hydrogen, an amino protecting group, —(CH$_2$)$_n$—X, —(CH$_2$)$_n$—OR,

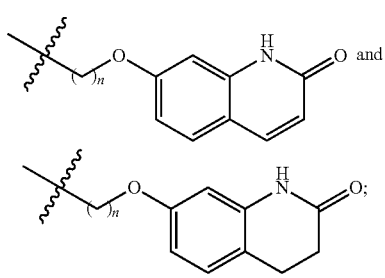

n is an integer from 1 to 6;

X is a leaving group;

R is selected from H and a hydroxyl protecting group;

R² is selected from —CHO, —CN, —C(O)OR' and —C(O)X';

X' is halogen;

R' is selected from H, C$_1$-C$_6$ alkyl, C$_6$-C$_{10}$ aryl and (C$_6$-C$_{10}$)aryl(C$_1$-C$_6$)alkyl;

R³ is selected from C$_1$-C$_6$ alkyl, C$_6$-C$_{10}$ aryl, (C$_6$-C$_{10}$)aryl(C$_1$-C$_6$)alkyl, —C(O)OR", —C(S)OR" and —C(O)R"; and R" is selected from C$_1$-C$_6$ alkyl, C$_6$-C$_{10}$ aryl and (C$_6$-C$_{10}$)aryl(C$_1$-C$_6$)alkyl.

In another aspect, the invention is directed to a compound of formula (III), or a salt or solvate thereof (III)

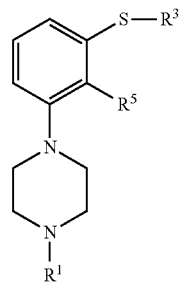

wherein

R¹ is selected from hydrogen, an amino protecting group, —(CH$_2$)$_n$—X, —(CH$_2$)$_n$—OR,

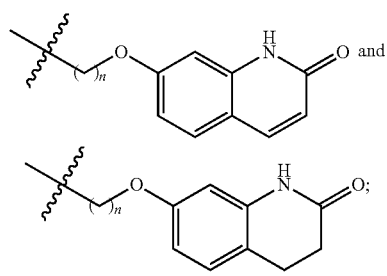

n is an integer from 1 to 6;

X is a leaving group;

R is selected from H and a hydroxyl protecting group;

R⁴ is selected from halogen and —OR';

R' is selected from C$_1$-C$_6$ alkyl, C$_6$-C$_{10}$ aryl and (C$_6$-C$_{10}$)aryl(C$_1$-C$_6$)alkyl;

R³ is selected from C$_1$-C$_6$ alkyl, C$_6$-C$_{10}$ aryl, (C$_6$-C$_{10}$)aryl(C$_1$-C$_6$)alkyl, —C(O)OR", —C(S)OR" and —C(O)R"; and R" is selected from C$_1$-C$_6$ alkyl, C$_6$-C$_{10}$ aryl and (C$_6$-C$_{10}$)aryl(C$_1$-C$_6$)alkyl.

In another aspect, the invention is directed to a compound of formula (IV), or a salt or solvate thereof (IV)

wherein

R¹ is selected from hydrogen, an amino protecting group, —(CH$_2$)$_n$—X, —(CH$_2$)$_n$—OR, n is an integer from 1 to 6;

X is a leaving group;

R is selected from H and a hydroxyl protecting group;

R³ is selected from C$_1$-C$_6$ alkyl, C$_6$-C$_{10}$ aryl, (C$_6$-C$_{10}$)aryl(C$_1$-C$_6$)alkyl, —C(O)OR", —C(S)OR" and —C(O)R";

R" is selected from C$_1$-C$_6$ alkyl, C$_6$-C$_{10}$ aryl and (C$_6$-C$_{10}$)aryl(C$_1$-C$_6$)alkyl;

R⁵ is selected from —CHO, —CN, —C(O)OR'" and —C(O)X";

X''' is halogen; and

R'''' is selected from H, $C_1$-$C_6$ alkyl, $C_6$-$C_{10}$ aryl and ($C_6$-$C_{10}$)aryl($C_1$-$C_6$)alkyl, with the proviso that when $R^1$ is hydrogen and $R^3$ is methyl, then $R^6$ is not —CN.

DETAILED DESCRIPTION OF THE INVENTION

The term "$C_1$-$C_6$ alkyl" refers to a linear or branched alkane derivative containing from 1 to 6, more preferably from 1 to 3 ("$C_1$-$C_3$ alkyl"), carbon atoms and which is bound to the rest of the molecule through a single bond. Illustrative examples of alkyl groups include methyl, ethyl, propyl, butyl, pentyl, hexyl, etc.

The term "halogen" refers to bromo, chloro, iodo or fluoro.

The term "$C_6$-$C_{10}$ aryl" refers to an aromatic group having between 6 and 10 carbon atoms, comprising 1 or 2 aromatic nuclei bound by means of a carbon-carbon bond or fused, including for example phenyl, naphthyl and diphenyl.

The term "($C_6$-$C_{10}$)aryl($C_1$-$C_6$)alkyl" refers to an alkyl group as defined above substituted with an aryl group as defined above. Examples of such groups include benzyl, phenylethyl, phenylpropyl, naphthylmethyl, etc.

The term "$C_3$-$C_7$ cycloalkyl" refers to a radical derived from cycloalkane containing from 3 to 7, preferably from 3 to 6 ("$C_3$-$C_6$ cycloalkyl") carbon atoms. Illustrative examples of cycloalkyl groups include cyclopropyl, cyclobutyl, cyclopentyl, cyclohexyl, etc.

The term "$C_1$-$C_6$ alkoxy" designates an alkyl group as defined above having between 1 and 6 carbon atoms, more preferably between 1 and 3 carbon atoms ("$C_1$-$C_3$ alkoxy"), linked to the rest of the molecule through oxygen. Examples of alkoxy include methoxy, ethoxy, isopropoxy, tertbutoxy, and the like.

The term "heterocyclyl" refers to a saturated or partially unsaturated monocyclic or bicyclic system containing from 3 to 10, preferably 5 to 7, ring atoms containing one or more, specifically one, two, three or four ring heteroatoms independently selected from N, O, and S, and the remaining ring atoms being carbon.

The term "heteroaryl" refers to an aromatic monocyclic or bicyclic system containing from 3 to 10, preferably 5 to 7, ring atoms containing one or more, specifically one, two, three or four ring heteroatoms independently selected from O, N and S, and the remaining ring atoms being carbon.

The term "hydroxyl protecting group" (HPG) refers to a group blocking the OH function for subsequent reactions that can be removed under controlled conditions.

Hydroxyl protecting groups are well known in the art. Illustrative examples of hydroxyl protecting groups have been described by Green T W et al. in "Protective Groups in Organic Synthesis", 3rd Edition (1999), Ed. John Wiley & Sons. Virtually any hydroxyl protecting group can be used to put the invention into practice. Illustrative, non-limiting examples of HPGs include:

silyl ethers [—Si(R)(R')(R'')]. R, R' and R'' can be independently selected from $C_1$-$C_6$ alkyl, $C_3$-$C_7$ cycloalkyl, $C_6$-$C_{10}$ aryl, $C_1$-$C_6$ alkoxy and halogen. Examples of silyl ethers include trimethylsilyl ether, triethylsilyl ether, tert-butyldimethylsilyl ether, tert-butyldiphenylsilyl ether, tri-isopropylsilyl ether, diethylisopropylsilyl ether, hexyldimethylsilyl ether, triphenylsilyl ether, di-tert-butylmethylsilyl ether;

ethers [—R], including alkoxy and aryloxy methyl ethers [—CH$_2$—OR]. R can be selected from $C_1$-$C_6$ alkyl, $C_6$-$C_{10}$ aryl and ($C_6$-$C_{10}$)aryl($C_1$-$C_6$)alkyl. Examples of ethers include methyl ether, tert-butyl ether, benzyl ether, p-methoxybenzyl ether, 3,4-dimethoxybenzyl ether, trityl ether, allyl ether, methoxymethyl ether, 2-methoxyethoxymethyl ether, benzyloxymethyl ether, p-methoxybenzyloxymethyl ether, 2-(trimethylsilyl)ethoxymethyl ether; tetrahydropyranyl and related ethers;

esters [—COR]. R can be selected from $C_1$-$C_6$ alkyl, $C_6$-$C_{10}$ aryl and ($C_6$-$C_{10}$)aryl($C_1$-$C_6$)alkyl. Examples of esters include acetate ester, benzoate ester, pivalate ester, methoxyacetate ester, chloroacetate ester, levulinate ester; and carbonates [—COOR]. R can be selected from $C_1$-$C_6$ alkyl, $C_6$-$C_{10}$ aryl and ($C_6$-$C_{10}$)aryl($C_1$-$C_6$)alkyl. Examples of carbonates include benzyl carbonate, p-nitrobenzyl carbonate, tert-butyl carbonate, 2,2,2-trichloroethyl carbonate, 2-(trimethylsilyl)ethyl carbonate, allyl carbonate.

The term "amino protecting group" (APG) refers to a group blocking the NH function for subsequent reactions that can be removed under controlled conditions. Amino protecting groups are well known in the art. Illustrative examples of amino protecting groups have been described by Green T W et al. in "Protective Groups in Organic Synthesis", 3rd Edition (1999), Ed. John Wiley & Sons. Virtually any amino protecting group can be used to put the invention into practice. Illustrative, non-limiting examples of APGs include:

carbamates [—COOR]. R can be selected from $C_1$-$C_6$ alkyl, $C_1$-$C_6$ alkenyl, $C_3$-$C_7$ cycloalkyl, $C_6$-$C_{10}$ aryl, ($C_6$-$C_{10}$)aryl($C_1$-$C_6$)alkyl, 3- to 10-membered heterocyclyl, 3- to 10-membered heteroaryl. Examples of carbamates include methyl carbamate, t-butyl carbamate, benzyl carbamate, 9-fluorenilmetil carbamate, trichloroethyl carbamate, trimethylsilyl carbamate;

amides [—COR]. R can be selected from $C_1$-$C_6$ alkyl, $C_1$-$C_6$ alkenyl, $C_3$-$C_7$ cycloalkyl, $C_6$-$C_{10}$ aryl, ($C_6$-$C_{10}$)aryl($C_1$-$C_6$)alkyl, 3- to 10-membered heterocyclyl, 3- to 10-membered heteroaryl. Examples of amides include formamide, acetamide, phenylacetamide, haloacetamide, benzamide, picolinamide;

amines [—R]. R can be selected from $C_1$-$C_6$ alkyl, $C_6$-$C_{10}$ aryl and ($C_6$-$C_{10}$)aryl($C_1$-$C_6$)alkyl. Examples of amines include methyl amine, tert-butyl amine, benzyl amine, allyl amine, methoxymethyl amine, triphenylmethyl amine, dinitrophenyl amine, methoxyphenyl amine; and silyl amines [—Si(R)(R')(R'')]. R, R' and R'' can be independently selected from $C_1$-$C_6$ alkyl, $C_3$-$C_7$ cycloalkyl, $C_6$-$C_{10}$ aryl, $C_1$-$C_6$ alkoxy and halogen. Examples of silyl amines include trimethylsilyl amine, triethylsilyl amine, tert-butyldimethylsilyl amine, tert-butyldiphenylsilyl amine, tri-isopropylsilyl amine, triphenylsilyl amine.

The term "leaving group" refers to a functional group or an atom that can be displaced by another functional group in a substitution reaction, such as a nucleophilic substitution reaction. Suitable leaving groups are well known in the art. In a particular embodiment, the leaving group is selected from halogen, $C_1$-$C_6$ alkylsulfonates, $C_6$-$C_{10}$ arylsulfonates and $C_1$-$C_6$alkyl$C_6$-$C_{10}$arylsulfonates, such as chloro, bromo, iodo, mesylate, triflate, tosylate, nosylate and the like.

As understood in this technical area, there may be a certain degree of substitution in the aforementioned radicals. Therefore, there may be substitution in any of the groups of the present invention. The previous groups can be substituted in one or more available positions with one or more substituents. Said substituents include, for example and in non-limiting sense, $C_{1-6}$ alkyl, $C_{3-7}$ cycloalkyl, $C_6$-$C_{10}$ aryl, 3- to 10-membered heterocyclyl, 3- to 10-membered heteroaryl, halogen, —CN, $NO_2$, $CF_3$, —N($R_a$)($R_b$), —$OR_c$, —$SR_d$, —C(O)$R_e$, —C(O)O$R_f$, —C(O)N($R_g$)($R_h$), —OC(O)$R_i$; wherein $R_a$, $R_b$, $R_c$, $R_d$, $R_e$, $R_f$, $R_g$, $R_h$ and $R_i$ are independently selected from hydrogen, $C_1$-$C_6$ alkyl, $C_6$-$C_{10}$ aryl, 3- to 10-membered heterocyclyl, 3- to 10-membered heteroaryl and trifluoromethyl.

The invention also provides "salts" of the compounds described in the present description. By way of illustration, said salts can be acid addition salts, base addition salts or metal salts, and can be synthesized from the parent compounds containing a basic or acid moiety by means of conventional chemical processes known in the art. Such salts are generally prepared, for example, by reacting the free acid or base forms of said compounds with a stoichiometric amount of the suitable base or acid in water or in an organic solvent or in a mixture of the two. Non-aqueous media such as ether, ethyl acetate, ethanol, acetone, isopropanol or acetonitrile are generally preferred. Illustrative examples of said acid addition salts include inorganic acid addition salts such as, for example, hydrochloride, hydrobromide, hydroiodide, sulfate, nitrate, phosphate, etc., organic acid addition salts such as, for example, acetate, maleate, fumarate, citrate, oxalate, succinate, tartrate, malate, mandelate, methanesulfonate, p-toluenesulfonate, camphorsulfonate, etc. Illustrative examples of base addition salts include inorganic base salts such as, for example, ammonium salts and organic base salts such as, for example, ethylenediamine, ethanolamine, N,N-dialkylenethanolamine, triethanolamine, glutamine, amino acid basic salts, etc. Illustrative examples of metal salts include, for example, sodium, potassium, calcium, magnesium, aluminum and lithium salts. In a particular embodiment, the salt is an acid addition salt, such as hydrochloride, sulfate and sodium sulfate.

Likewise, the compounds described in the present description can be obtained both as free compounds or as solvates (e.g., hydrates, alcoholates, etc.), both forms being included within the scope of the present invention. The solvation methods are generally known in the state of the art. Preferably, the solvate is a hydrate.

The term "organic solvent" includes for example cyclic and acyclic ethers (e.g. $Et_2O$, $iPr_2O$, 1,4-dioxane, tetrahydrofuran, methyltetrahydrofuran), hydrocarbonated solvents (e.g. pentane, hexane), halogenated solvents (e.g. dichloromethane, chloroform), aromatic solvents (e.g. toluene, xylene), esters (e.g. EtOAc), amides (e.g. DMF, DMA), nitriles (e.g. acetonitrile), alcohols (e.g. methanol, ethanol, propanol, isopropanol) and mixtures thereof.

In a first aspect the invention is directed to a process for preparing a compound of formula (I), or a salt or solvate thereof

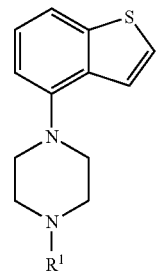

(I)

wherein
$R^1$ is selected from hydrogen, an amino protecting group, —$(CH_2)_n$—X, —$(CH_2)_n$—OR,

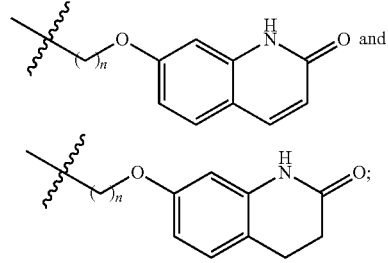

n is an integer from 1 to 6;
X is a leaving group;
R is selected from H and a hydroxyl protecting group;
which process comprises cyclization of a compound of formula (II), or a salt or solvate thereof

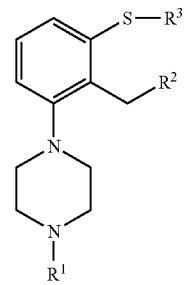

(II)

wherein
$R^1$ is as defined above;
$R^2$ is selected from —CHO, —CN, —C(O)OR' and —C(O)X';
X' is halogen;
R' is selected from H, $C_1$-$C_6$ alkyl, $C_6$-$C_{10}$ aryl and ($C_6$-$C_{10}$)aryl($C_1$-$C_6$)alkyl;
$R^3$ is selected from $C_1$-$C_6$ alkyl, $C_6$-$C_{10}$ aryl, ($C_6$-$C_{10}$)aryl($C_1$-$C_6$)alkyl, —C(O)OR", —C(S)OR" and —C(O)R"; and
R" is selected from $C_1$-$C_6$ alkyl, $C_6$-$C_{10}$ aryl and ($C_6$-$C_{10}$)aryl($C_1$-$C_6$)alkyl.

In a second aspect, the invention is directed to a process for preparing a compound of formula (I), or a salt or solvate thereof, as defined above which comprises cyclization of a compound of formula (III), or a salt or solvate thereof (III)

[Structure: benzene ring with S—R³ substituent, vinyl group with R⁴, connected to piperazine with N-R¹]

wherein
R¹ is as defined above;
R⁴ is selected from halogen and —OR';
R' is selected from $C_1$-$C_6$ alkyl, $C_6$-$C_{10}$ aryl and ($C_6$-$C_{10}$)aryl($C_1$-$C_6$)alkyl;
R³ is selected from $C_1$-$C_6$ alkyl, $C_6$-$C_{10}$ aryl, ($C_6$-$C_{10}$)aryl($C_1$-$C_6$)alkyl, —C(O)OR", —C(S)OR" and —C(O)R"; and
R" is selected from $C_1$-$C_6$ alkyl, $C_6$-$C_{10}$ aryl and ($C_6$-$C_{10}$)aryl($C_1$-$C_6$)alkyl.

In an embodiment, n is an integer selected from 2 to 6; preferably from 3 to 5; more preferably n is 4.

In an embodiment, R¹ is selected from hydrogen, an amino protecting group, —(CH₂)₄—X, —(CH₂)₄—OR,

[Structure showing chain-O-quinolinone and chain-O-dihydroquinolinone]

In a particular embodiment, R¹ is selected from hydrogen, a carbamate or amide or amine protecting group, and

[Structure showing chain-O-quinolinone and chain-O-dihydroquinolinone]

Preferably, R¹ is selected from hydrogen, methyl, benzyl, formyl, acetyl, benzoyl, t-butoxycarbonyl, benzyloxycarbonyl, 9-fluorenylmethoxycarbonyl,

[Structure showing chain-O-quinolinone]

-continued

[Structure showing chain-O-dihydroquinolinone]

More preferably, R¹ is selected from hydrogen, t-butoxycarbonyl, benzyl and

[Structure showing chain-O-quinolinone]

In a particular embodiment, R² is —CHO.

In an embodiment, R⁴ is —OR', wherein R' is as defined above. In a preferred embodiment, R' is selected from $C_1$-$C_6$ alkyl, more preferably $C_1$-$C_4$ alkyl. In a particular embodiment, R⁴ is —OMe.

In an embodiment, R³ is selected from $C_1$-$C_6$ alkyl, $C_6$-$C_{10}$ aryl, ($C_6$-$C_{10}$)aryl($C_1$-$C_6$)alkyl; more preferably it is selected from $C_1$-$C_6$ alkyl, phenyl and benzyl. In a particular embodiment, R³ is selected from $C_1$-$C_6$ alkyl, such as tBu and nPr.

In a particular embodiment, n is 4 and R² is —CHO (for compound of formula II) or R⁴ is —OR', wherein R' is selected from $C_1$-$C_6$ alkyl, $C_6$-$C_{10}$ aryl and ($C_6$-$C_{10}$)aryl($C_1$-$C_6$)alkyl (for compound of formula III). In an embodiment, n is 4 and R² is —CHO (for compound of formula II) or R⁴ is —O$C_1$-$C_6$ alkyl (for compound of formula III).

In another embodiment, n is 4, R² is —CHO (for compound of formula II) or R⁴ is —O$C_1$-$C_6$ alkyl (for compound of formula III) and R³ is $C_1$-$C_6$ alkyl. In an embodiment, n is 4, R² is —CHO (for compound of formula II) or R⁴ is —OMe (for compound of formula III) and R³ is selected from tBu and nPr.

In a preferred embodiment, the compound of formula (I) is selected from (1-benzothiophen-4-yl)piperazine and Brexpiprazole, or a salt or solvate thereof. Preferably, the compound of formula (I) is Brexpiprazole, or a salt or solvate thereof. More preferably, the compound of formula (I) is Brexpiprazole.

Cyclization Reaction

In a particular embodiment, the cyclization reaction of a compound of formula (II) or (III), or a salt or solvate thereof, is carried out in the presence of an acid.

Suitable acids include organic, inorganic acids and mixtures thereof. Examples of organic acids include acetic acid, trifluoroacetic acid, methanesulfonic acid, trifluoromethanesulfonic acid, formic acid, propionic acid, butyric acid, malic acid, citric acid, benzoic acid, p-toluenesulfonic acid, oxalic acid and succinic acid. Examples of inorganic acids include hydrochloric acid, hydrobromic acid, hydrofluoric acid, perchloric acid, sulfuric acid, nitric acid and phosphoric acid. In a particular embodiment, the acid is selected from acetic acid, trifluoroacetic acid, methanesulfonic acid, trifluoromethanesulfonic acid, hydrochloric acid, hydrobromic acid, perchloric acid, sulfuric acid and mixtures thereof.

In a particular embodiment, the cyclization reaction is carried out at a temperature between −40° C. and 150° C., preferably between −20° C. and 100° C., more preferably between −10° C. and 80° C.

Preferably, the cyclization reaction is carried out in the presence of an organic solvent, such as for example a cyclic or acyclic ether (e.g. Et$_2$O, iPr$_2$O, tBu$_2$O, 1,4-dioxane, tetrahydrofuran, methyltetrahydrofuran), a hydrocarbonated solvent (e.g. pentane, hexane), a halogenated solvent (e.g. dichloromethane, chloroform), an alcohol (e.g. methanol, ethanol, propanol), an aromatic solvent (e.g. toluene, xylene), an amide (DMF, DMA) or mixtures thereof. In a particular embodiment, the reaction is performed in the presence of a halogenated solvent, such as dichloromethane. In an embodiment, the cyclization reaction is carried out in the presence of an organic solvent and water.

In a particular embodiment, the cyclization reaction is performed at a temperature between −20° C. and 100° C., in the presence of an organic solvent and an acid selected from acetic acid, trifluoroacetic acid, methanesulfonic acid, trifluoromethanesulfonic acid, formic acid, propionic acid, butyric acid, malic acid, citric acid, benzoic acid, p-toluenesulfonic acid, oxalic acid, succinic acid, hydrochloric acid, hydrobromic acid, hydrofluoric acid, perchloric acid, sulfuric acid, nitric acid and phosphoric acid.

Further Transformations of the Compound of Formula (I)

Depending on the desired compound of formula (I), it might be necessary to further transform the compound of formula (I) obtained after cyclization of the compound of formula (II) or (III).

In a particular embodiment, after cyclization of the compound of formula (II) or (III), or a salt or solvate thereof, it is obtained a compound of formula (I), or a salt or solvate thereof, wherein R$^1$ is selected from hydrogen, an amino protecting group, —(CH$_2$)$_n$—X and —(CH$_2$)$_n$—OR; n is an integer from 1 to 6; X is a leaving group; and R is selected form H and a hydroxyl protecting group; which is further converted into a compound of formula (I), or a salt or solvate thereof, wherein R$^1$ is selected from

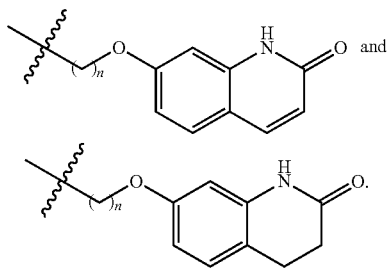

In a preferred embodiment, the process further comprises converting a compound of formula (I), or a salt or solvate thereof, wherein R$^1$ is selected from hydrogen, an amino protecting group, —(CH$_2$)$_4$—X and —(CH$_2$)$_4$—OR; X is a leaving group; and R is selected from H and a hydroxyl protecting group; into a compound of formula (I), or a salt or solvate thereof, wherein R$^1$ is selected from

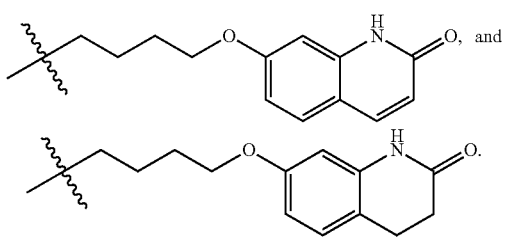

Said transformations can be carried out by conventional means known in the art (e.g. M. B. Smith, J. March, March's Advanced Organic Chemistry, Wiley-Interscience, 5$^{th}$ ed., pp. 1541-1542).

For instance, a compound of formula (I), or a salt or solvate thereof, wherein R$^1$ is hydrogen can be converted into a compound of formula (I), or a salt or solvate thereof, wherein R$^1$ is selected from

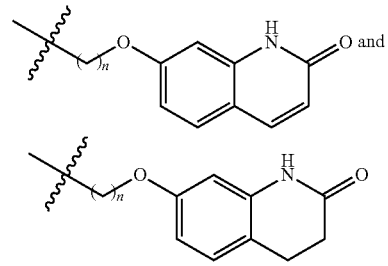

by a method as disclosed in EP1869025 or in WO02013/015456. In an embodiment, a compound of formula (I), or a salt or solvate thereof, wherein R$^1$ is hydrogen is further reacted with a compound of formula (V), or a salt or solvate thereof

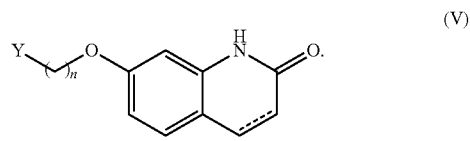

(V)

wherein
Y is a leaving group; and
⸗ is a single or a double bond, to yield a compound of formula (I), or a salt or solvate thereof, wherein R$^1$ is selected from

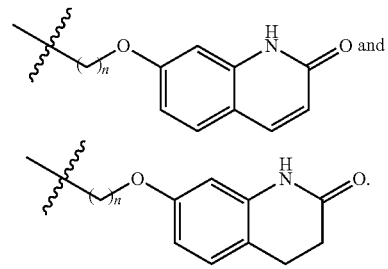

In a particular embodiment, Y is selected from halogen, C$_1$-C$_6$ alkylsulfonates and C$_6$-C$_{10}$ arylsulfonates, such as chloro, mesylate, triflate and tosylate. Preferably, ⸗ denotes a double bond.

The reaction can be carried out in the presence of a basic compound and an organic solvent.

If a compound of formula (I), or a salt or solvate thereof, wherein R$^1$ is an amino protecting group is obtained after the cyclization reaction, it can be first converted into a compound of formula (I), or a salt or solvate thereof, wherein R$^1$ is hydrogen through deprotection of the amine protecting group by any conventional means known in the art (e.g. T. W. Green et al. in Protective Groups in Organic Synthesis, 3$^{rd}$ Ed., 1999, Ed. John Wiley & Sons).

A compound of formula (I), or a salt or solvate thereof, wherein R¹ is —(CH$_2$)$_n$—X or —(CH$_2$)$_n$—OR can be converted into a compound of formula (I), or a salt or solvate thereof, wherein R¹ is selected from

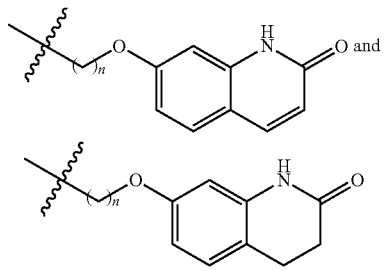

by a method as disclosed in EP1869025. In an embodiment, a compound of formula (I), or a salt or solvate thereof, wherein R¹ is —(CH$_2$)$_n$—X or —(CH$_2$)$_n$—OR is further reacted with a compound of formula (VI), or a salt or solvate thereof

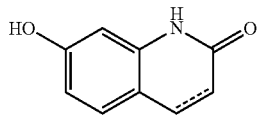

⋯ is a single or a double bond, to yield a compound of formula (I), or a salt or solvate thereof, wherein R¹ is selected from

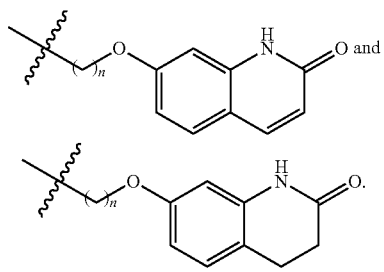

In a particular embodiment, R¹ in the starting compound of formula (I) is selected from —(CH$_2$)$_n$—OH and —(CH$_2$)$_n$—X wherein X is selected from halogen, C$_1$-C$_6$ alkylsulfonates and C$_6$-C$_{10}$ arylsulfonates, such as chloro, mesylate, triflate and tosylate. Preferably, ⋯ denotes a double bond.

The reaction can be carried out in the presence of an organic solvent and a basic compound or a condensing agent.

Compounds of formula (V) and (VI) are known or can be easily produced from known compounds.

Preparation of Compounds of Formula (II)

In a particular embodiment, the compound of formula (II), or a salt or solvate thereof, is obtained from a compound of formula (IV), or a salt or solvate thereof

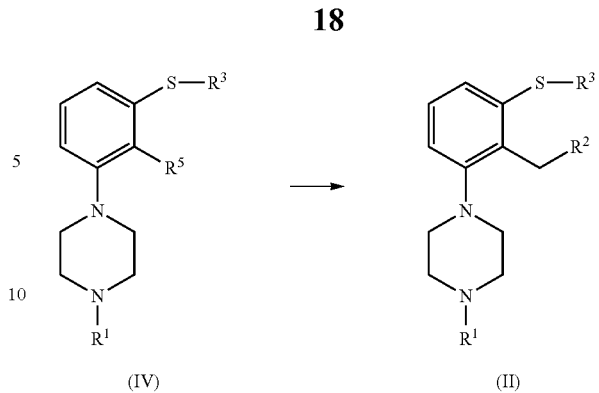

wherein
R¹ and R³ are as defined in claim 1;
R⁵ is selected from —CHO, —CN, —C(O)OR''' and —C(O)X'';
X'' is halogen; and
R''' is selected from H, C$_1$-C$_6$ alkyl, C$_6$-C$_{10}$ aryl and (C$_6$-C$_{10}$)aryl(C$_1$-C$_6$)alkyl.

In an embodiment, the compound of formula (II), or a salt or solvate thereof, is obtained by a process comprising homologation of a compound of formula (IV), or a salt or solvate thereof.

Homologation reactions and suitable reaction conditions are known in the art (e.g. M. B. Smith, J. March, March's Advanced Organic Chemistry, Wiley-Interscience, 5$^{th}$ ed., pp. 1541-1542; Science of Synthesis: Houben-Weyl methods of molecular transformations, Thieme).

For instance, a compound of formula (IV) wherein R⁵ is —C(O)OR''', or a salt or solvate thereof, can be homologated to a compound of formula (II) wherein R² is —C(O)OR', or a salt or solvate thereof, through Arndt-Eistert reaction or through Kowalski ester homologation.

In a preferred embodiment, R⁵ is —CHO. Homologation reactions of aldehydes are well-known in the art (e.g. Science of Synthesis: Houben-Weyl methods of molecular transformations, Category 4: Compounds with two carbon-heteroatom bonds: Aldehydes, Chapter 25.1.10). For instance, a compound of formula (IV) wherein R⁵ is —CHO, or a salt or solvate thereof, can be homologated to a compound of formula (II) wherein R² is —CHO, or a salt or solvate thereof, via Darzens reaction, via addition of a nitroalkane followed by Nef reaction, via cyanation followed by reduction of the nitrile, through reaction with a dihalomethane or diazomethane, via Wittig-type reaction followed by hydrolysis, via Corey-Fuchs reaction followed by hydroboration, via Peterson-type alkenylation followed by hydrolysis, via Julia-type alkenylation followed by hydrolysis, etc.

In an embodiment, a compound of formula (II) wherein R² is —CHO, or a salt or solvate thereof, is obtained by homologation of a compound of formula (IV) wherein R⁵ is —CHO, or a salt or solvate thereof, via Darzens reaction. In a particular embodiment, a compound of formula (IV) wherein R⁵ is —CHO, or a salt or solvate thereof, is reacted with a compound of formula (VII) Hal C(O)OR Hal⌒C(O)OR     (VII)

wherein

Hal means halogen, preferably Cl; and

R is selected from $C_1$-$C_6$ alkyl, $C_6$-$C_{10}$ aryl and $(C_6$-$C_{10})$aryl$(C_1$-$C_6)$alkyl, preferably Me or Et;

to yield a compound of formula (VIII)

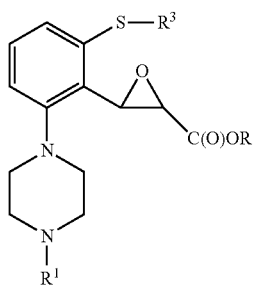

(VIII)

wherein R, $R^1$ and $R^3$ are as defined above;

which is decarboxylated to yield a compound of formula (II) wherein $R^2$ is —CHO, or a salt or solvate thereof.

In another embodiment, a compound of formula (II) wherein $R^2$ is —CHO, or a salt or solvate thereof, is obtained by homologation of a compound of formula (IV) wherein $R^5$ is —CHO, or a salt or solvate thereof, via alkenylation reaction followed by hydrolysis of the double bond. In a particular embodiment, a compound of formula (IV) wherein $R^5$ is —CHO, or a salt or solvate thereof, is alkenylated as described below to yield a compound of formula (III), or a salt or solvate thereof, which is then hydrolyzed to a compound of formula (II) wherein $R^2$ is —CHO, or a salt or solvate thereof.

In another embodiment, a compound of formula (II), or a salt or solvate thereof, wherein $R^5$ is —CN is obtained from a compound of formula (XII), or a salt or solvate thereof

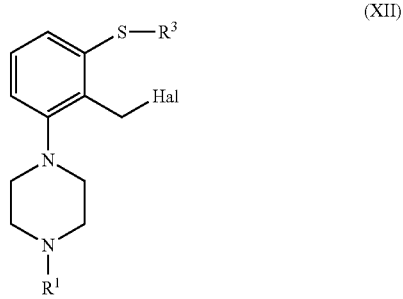

(XII)

For example, a compound of formula (II), or a salt or solvate thereof, wherein $R^5$ is selected —CN can be obtained through the following sequence

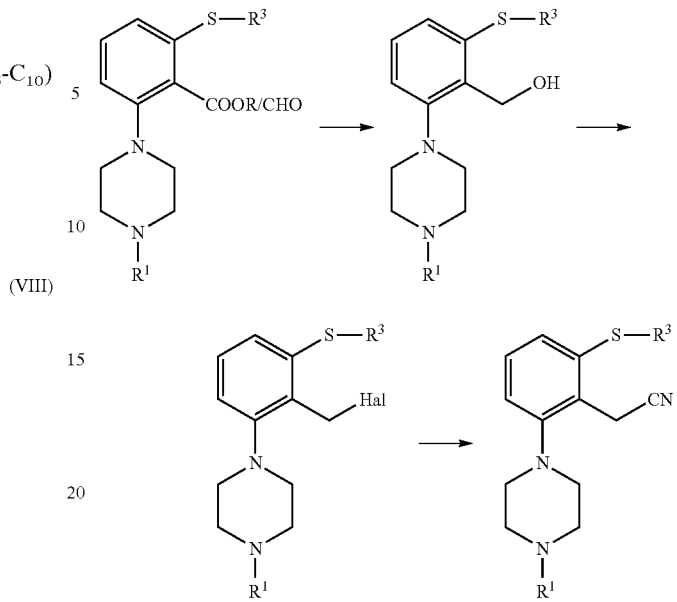

In turn, a compound of formula (II), or a salt or solvate thereof, wherein $R^5$ is —CN can be further transformed into a compound of formula (II), or a salt or solvate thereof, wherein $R^5$ is —CHO or —C(O)OR'" through reduction or hydrolysis, respectively.

In a particular embodiment, a compound of formula (II) wherein $R^2$ is —CHO, or a salt or solvate thereof, is obtained by hydrolysis of a compound of formula (III), or a salt or solvate thereof, in the presence of an acid.

Suitable acids include organic acids, inorganic acids and mixtures thereof. Examples of organic acids include acetic acid, trifluoroacetic acid, methanesulfonic acid, trifluoromethanesulfonic acid, formic acid, propionic acid, butyric acid, malic acid, citric acid, benzoic acid, p-toluenesulfonic acid, oxalic acid and succinic acid. Examples of inorganic acids include hydrochloric acid, hydrobromic acid, hydrofluoric acid, perchloric acid, sulfuric acid, nitric acid and phosphoric acid. In a particular embodiment, the acid is selected from acetic acid, trifluoroacetic acid, methanesulfonic acid, trifluoromethanesulfonic acid, hydrochloric acid, hydrobromic acid, perchloric acid, sulfuric acid and mixtures thereof.

Preferably, the hydrolisis reaction is carried out in the presence of an organic solvent and water. Suitable organic solvents include cyclic or acyclic ethers (e.g. $Et_2O$, $iPr_2O$, 1,4-dioxane, tetrahydrofuran, methyltetrahydrofuran), hydrocarbonated solvents (e.g. pentane, hexane), halogenated solvents (e.g. dichloromethane, chloroform), alcohols (e.g. methanol, ethanol, propanol), aromatic solvents (e.g. toluene), ester solvents (e.g. ethyl acetate) or mixtures thereof.

Preparation of Compounds of Formula (III)

In a particular embodiment, the compound of formula (III), or a salt or solvate thereof, is obtained by a process comprising alkenylation of a compound of formula (IV), or a salt or solvate thereof

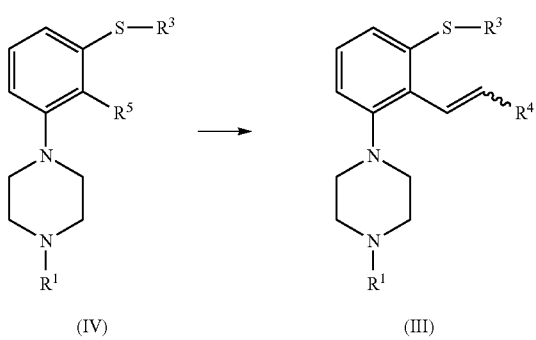

(IV)     (III)

wherein
R¹ and R³ are as defined in claim 1; and
R⁵ is —CHO.

Alkenylation reactions of aldehydes and suitable reaction conditions are known in the art (e.g. M. B. Smith, J. March, March's Advanced Organic Chemistry, Wiley-Interscience, 5$^{th}$ ed., pp. 1541-1542; Science of Synthesis: Houben-Weyl methods of molecular transformations, Thieme).

For instance, a compound of formula (IV) wherein R⁵ is —CHO, or a salt or solvate thereof, can be alkenylated to a compound of formula (II), or a salt or solvate thereof, through Wittig reaction, Julia olefination, Peterson olefination, Takai olefination, Stork-Wittig olefination and the like.

In an embodiment, a compound of formula (III), or a salt or solvate thereof, wherein R⁴ is —OR' is obtained by alkenylation of a compound of formula (IV) wherein R⁵ is —CHO, or a salt or solvate thereof, via Wittig-type reaction. In a particular embodiment, a compound of formula (IV) wherein R⁵ is —CHO, or a salt or solvate thereof, is reacted with a compound of formula (VIII), (IX) or (X)

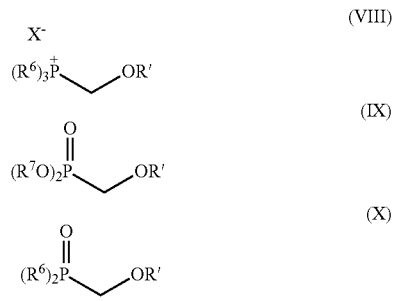

wherein
R' is as defined above;
X is halogen; and
each R⁶ is selected from $C_6$-$C_{10}$ aryl, preferably Ph; and
each R⁷ is selected from $C_1$-$C_6$ alkyl and ($C_6$-$C_{10}$)aryl ($C_1$-$C_6$)alkyl, preferably Me or Et;
in the presence of a base to yield a compound of formula (III) wherein R⁴ is —OR', or a salt or solvate thereof.

Suitable bases include organolithium bases, alkali metal hydrides and alkali metal alcoholates, such as e.g. nBuLi, tBuLi, sBuLi, MeLi, PhLi, LDA, NaH, NaOtBu, KOtBu, NaOMe, NaOEt.

Preferably, the reaction is carried out in the presence of an organic solvent, such as for example a cyclic or acyclic ether (e.g. $Et_2O$, $iPr_2O$, $tBu_2O$, 1,4-dioxane, tetrahydrofuran, methyltetrahydrofuran), a hydrocarbonated solvent (e.g. pentane, hexane), a halogenated solvent (e.g. dichloromethane, chloroform), an aromatic solvent (e.g. toluene, xylene), dimethylformamide, dimethylacetamide or mixtures thereof. In a particular embodiment, the reaction is performed in the presence of an ether, such as THF. In an embodiment, the reaction is carried out at a temperature between −20° C. and 150° C., preferably between 0° C. and 100° C.

In an embodiment, a compound of formula (III), or a salt or solvate thereof, wherein R⁴ is halogen is obtained by alkenylation of a compound of formula (IV) wherein R⁵ is —CHO, or a salt or solvate thereof, via Takai olefination or Stork-Wittig olefination.

Preparation of Compounds of Formula (IV)

In a particular embodiment, the compound of formula (IV), or a salt or solvate thereof, is obtained by reaction of a compound of formula (XI), or a salt or solvate thereof

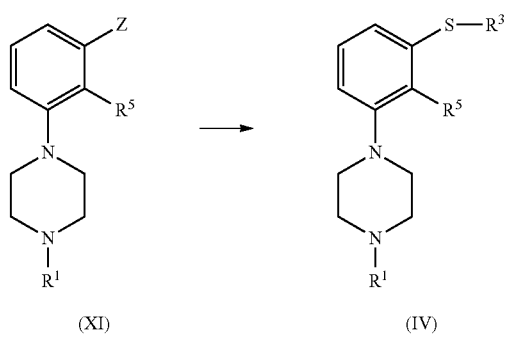

(XI)     (IV)

wherein
Z is selected from halogen and $NO_2$, preferably Cl; and
R¹ and R⁵ are as defined above;
with a thiol of formula HS—R³, wherein R³ is as defined above, in the presence of a base.

Suitable bases include e.g. alkali metal hydroxides, alkali metal carbonates, alkali metal bicarbonates, alkaline earth metal hydroxides, alkaline earth metal carbonates, alkali metal hydrides, alkali metal alkoxides, tertiary amines and mixtures thereof, such as sodium hydroxide, potassium hydroxide, calcium hydroxide, magnesium hydroxide, sodium hydride, potassium carbonate, sodium carbonate and cesium carbonate.

Preferably, the reaction is carried out in the presence of an organic solvent, such as for example a cyclic or acyclic ether (e.g. $Et_2O$, $iPr_2O$, $tBu_2O$, 1,4-dioxane, tetrahydrofuran, methyltetrahydrofuran), a hydrocarbonated solvent (e.g. pentane, hexane), a halogenated solvent (e.g. dichloromethane, chloroform), an aromatic solvent (e.g. toluene, xylene), dimethylformamide, dimethylacetamide or mixtures thereof. In a particular embodiment, the reaction is performed in the presence of an ether, such as THF. In an embodiment, the reaction is carried out at a temperature between −20° C. and 150° C., preferably between 0° C. and 120° C.

Compounds of formula (XI) are known or can be easily produced from known compounds (e.g. U.S. Pat. No. 5,436,246, WO 2015/054976).

Synthesis of Brexpiprazole

In an embodiment, the compound of formula (I) is Brexpiprazole, or a salt or solvate thereof. Preferably, the compound of formula (I) is Brexpiprazole.

Therefore, in a particular embodiment, the invention refers to a process for preparing Brexpiprazole, or a salt or solvate thereof, which comprises cyclization in the presence of an acid of a compound of formula (IIa) or (IIIa), or a salt or solvate thereof

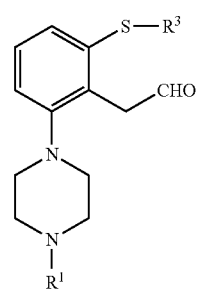

(IIa)

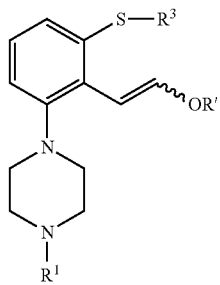

(IIIa)

wherein
R$^1$ is selected from hydrogen, an amino protecting group, —(CH$_2$)$_4$—X, —(CH$_2$)$_4$—OR, and

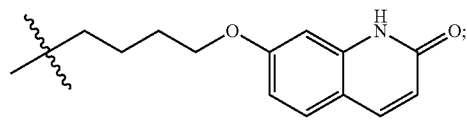 [SMILES: *CCCCOc1ccc2ccc(=O)[nH]c2c1]

X is a leaving group;
R is selected from H and a hydroxyl protecting group;
R$^3$ is selected from C$_1$-C$_6$ alkyl, C$_6$-C$_{10}$ aryl, (C$_6$-C$_{10}$)aryl(C$_1$-C$_6$)alkyl, —C(O)OR", —C(S)OR" and —C(O)R";
R" is selected from C$_1$-C$_6$ alkyl, C$_6$-C$_{10}$ aryl and (C$_6$-C$_{10}$) aryl(C$_1$-C$_6$)alkyl; and
R' is selected from C$_1$-C$_6$ alkyl, C$_6$-C$_{10}$ aryl and (C$_6$-C$_{10}$) aryl(C$_1$-C$_6$)alkyl.

In an embodiment, the invention refers to a process for preparing Brexpiprazole, or a salt or solvate thereof, which comprises cyclization in the presence of an acid of a compound of formula (IIa) or (IIIa) wherein R$^1$ is

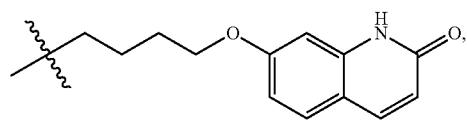 [SMILES: *CCCCOc1ccc2ccc(=O)[nH]c2c1]

or a salt or solvate thereof.

In another embodiment, the invention refers to a process for preparing Brexpiprazole, or a salt or solvate thereof, which comprises:

(i) cyclization in the presence of an acid of a compound of formula (IIa) or (IIIa) wherein R$^1$ is selected from hydrogen and an amino protecting group, or a salt or solvate thereof;
(ii) if needed, removal of the amino protecting group, to yield a compound of formula (I) wherein R$^1$ is hydrogen, or a salt or solvate thereof; and
(iii) reaction with a compound of formula (Va), or a salt or solvate thereof

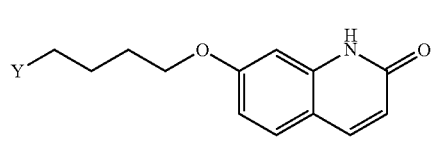

(Va)

wherein Y is a leaving group, in the presence of a basic compound.

In another embodiment, the invention refers to a process for preparing Brexpiprazole, or a salt or solvate thereof, which comprises:

(i) cyclization in the presence of an acid of a compound of formula (IIa) or (IIIa) wherein R$^1$ is selected from —(CH$_2$)$_4$—X and —(CH$_2$)$_4$—OR, or a salt or solvate thereof;
(ii) if needed, removal of the hydroxyl protecting group, to yield a compound of formula (I) wherein R$^1$ is selected from —(CH$_2$)$_4$—X and —(CH$_2$)$_4$—OH, or a salt or solvate thereof; and
(iii) reaction with a compound of formula (VIa), or a salt or solvate thereof

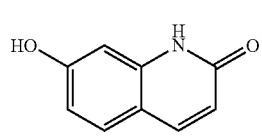

(VIa)

in the presence of a basic compound or a condensing agent.

Preferred embodiments for the cyclization reaction and for R$^1$, R$^3$, X, R, R', R", Y are as defined above.

In an embodiment, the compound of formula (IIa), or a salt or solvate thereof, is obtained from a compound of formula (IVa), or a salt or solvate thereof, via Darzens reaction. Preferably, by reaction of a compound of formula (IVa), or a salt or solvate thereof, with a compound of formula (VII) as defined above, followed by decarboxylation.

In an embodiment, the compound of formula (IIa), or a salt or solvate thereof, is obtained by hydrolysis of a compound of formula (IIIa), or a salt or solvate thereof.

In an embodiment, the compound of formula (IIIa), or a salt or solvate thereof, is obtained from a compound of formula (IVa), or a salt or solvate thereof, via Wittig-type reaction. Preferably, by reaction of a compound of formula (IVa), or a salt or solvate thereof, with a compound of formula (VIII), (IX) or (X) as defined above, in the presence of a base.

Preferred embodiments for the Darzens reaction, hydrolysis reaction and Wittig-type reaction are as defined above.

Intermediate Compounds

Compounds of formula (II), (III) and (IV), and their salts and solvates, are useful intermediates in the preparation of piperazine substituted benzo[b]thiophene compounds.

Therefore, in another aspect the invention is directed to a compound of formula (II), or a salt o solvate thereof

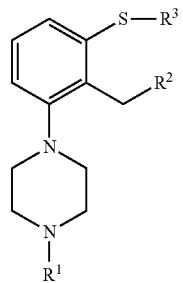
(II)

wherein $R^1$ is selected from hydrogen, an amino protecting group, —$(CH_2)_n$—X, —$(CH_2)_n$—OR,

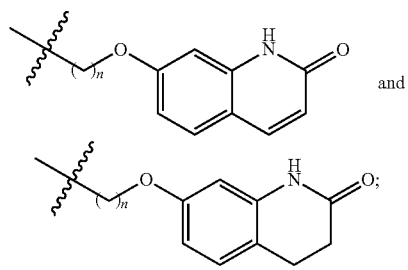
and;

n is an integer from 1 to 6;

X is a leaving group;

R is selected from H and a hydroxyl protecting group;

$R^2$ is selected from —CHO, —CN, —C(O)OR' and —C(O)X';

X' is halogen;

R' is selected from H, $C_1$-$C_6$ alkyl, $C_6$-$C_{10}$ aryl and ($C_6$-$C_{10}$)aryl($C_1$-$C_6$)alkyl;

$R^3$ is selected from $C_1$-$C_6$ alkyl, $C_6$-$C_{10}$ aryl, ($C_6$-$C_{10}$)aryl($C_1$-$C_6$)alkyl, —C(O)OR", —C(S)OR" and —C(O)R"; and R" is selected from $C_1$-$C_6$ alkyl, $C_6$-$C_{10}$ aryl and ($C_6$-$C_{10}$)aryl($C_1$-$C_6$)alkyl.

Preferred embodiments for $R^1$-$R^3$, n, X, X', R, R' and R" are as defined above. In a particular embodiment, the compound of formula (II) is a compound of formula (IIa), or a salt or solvate thereof

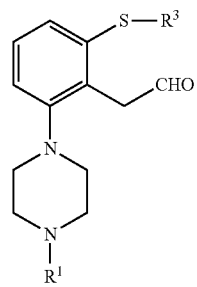
(IIa)

wherein $R^1$ is selected from hydrogen, an amino protecting group, —$(CH_2)_4$—X, —$(CH_2)_4$—OR,

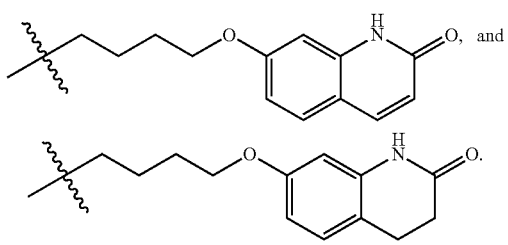
, and

X is a leaving group;

R is selected from H and a hydroxyl protecting group;

$R^3$ is selected from $C_1$-$C_6$ alkyl, $C_6$-$C_{10}$ aryl, ($C_6$-$C_{10}$)aryl($C_1$-$C_6$)alkyl, —C(O)OR", —C(S)OR" and —C(O)R"; and R" is selected from $C_1$-$C_6$ alkyl, $C_6$-$C_{10}$ aryl and ($C_6$-$C_{10}$)aryl($C_1$-$C_6$)alkyl.

In a preferred embodiment, the compound of formula (II) is selected from

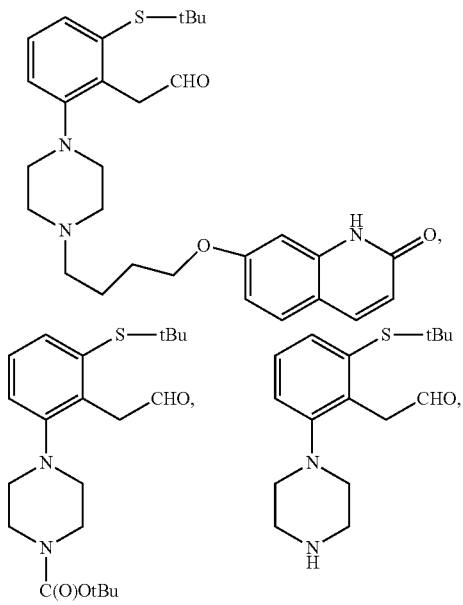

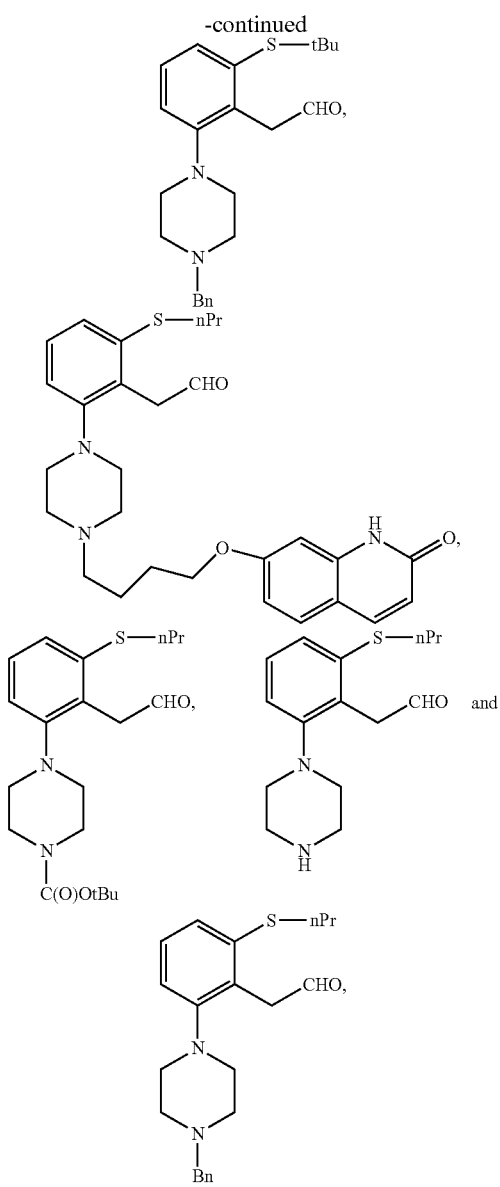

or a salt or solvate thereof.

In another aspect the invention is directed to a compound of formula (III), or a salt or solvate thereof

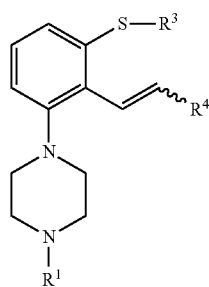

(III)

wherein
R$^1$ is selected from hydrogen, an amino protecting group, —(CH$_2$)$_n$—X, —(CH$_2$)$_n$—OR,

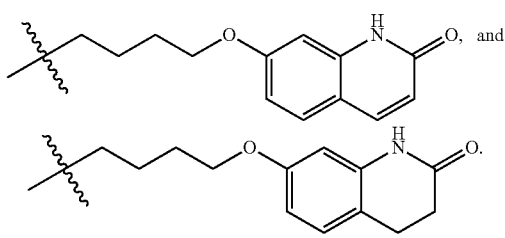

n is an integer from 1 to 6;
X is a leaving group;
R is selected from H and a hydroxyl protecting group;
R$^4$ is selected from halogen and —OR';
R' is selected from C$_1$-C$_6$ alkyl, C$_6$-C$_{10}$ aryl and (C$_6$-C$_{10}$) aryl(C$_1$-C$_6$)alkyl;
R$^3$ is selected from C$_1$-C$_6$ alkyl, C$_6$-C$_{10}$ aryl, (C$_6$-C$_{10}$)aryl (C$_1$-C$_6$)alkyl, —C(O)OR", —C(S)OR" and —C(O)R";
and
R" is selected from C$_1$-C$_6$ alkyl, C$_6$-C$_{10}$ aryl and (C$_6$-C$_{10}$) aryl(C$_1$-C$_6$)alkyl.

Preferred embodiments for R$^1$, R$^3$, R$^4$, n, X, R, R' and R" are as defined above. In a particular embodiment, the compound of formula (III) is a compound of formula (IIIa), or a salt or solvate thereof (IIIa)

wherein
R$^1$ is selected from hydrogen, an amino protecting group, —(CH$_2$)$_4$—X, —(CH$_2$)$_4$—OR, X is a leaving group;
R is selected from H and a hydroxyl protecting group;
R' is selected from C$_1$-C$_6$ alkyl, C$_6$-C$_{10}$ aryl and (C$_6$-C$_{10}$) aryl(C$_1$-C$_6$)alkyl;
R$^3$ is selected from C$_1$-C$_6$ alkyl, C$_6$-C$_{10}$ aryl, (C$_6$-C$_{10}$)aryl (C$_1$-C$_6$)alkyl, —C(O)OR", —C(S)OR" and —C(O)R";
and
R" is selected from C$_1$-C$_6$ alkyl, C$_6$-C$_{10}$ aryl and (C$_1$-C$_{10}$) aryl(C$_1$-C$_6$)alkyl.

In a preferred embodiment, the compound of formula (III) is selected from

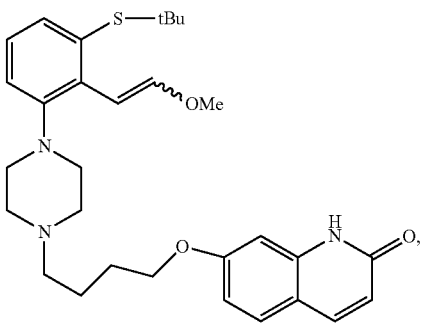

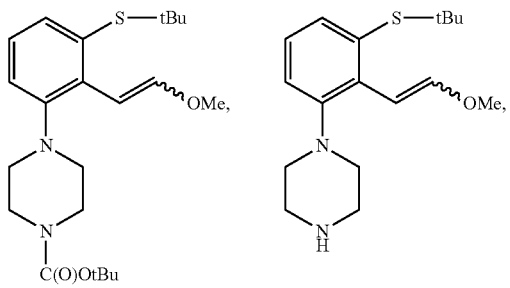

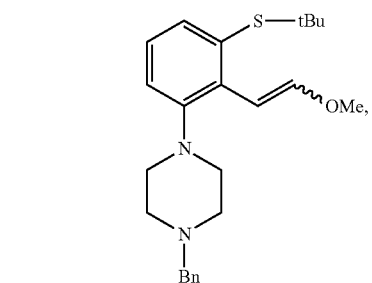

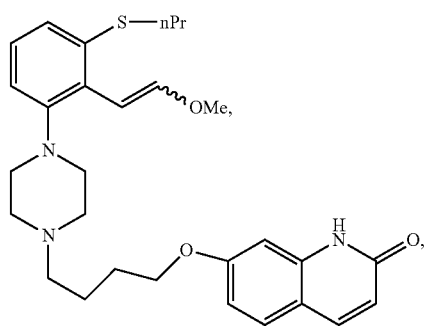

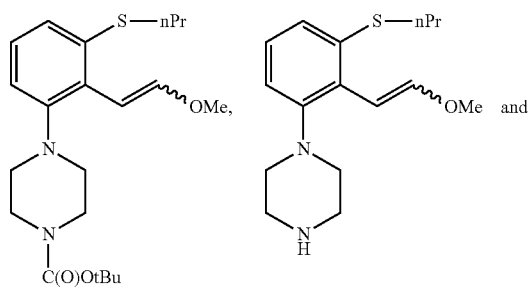

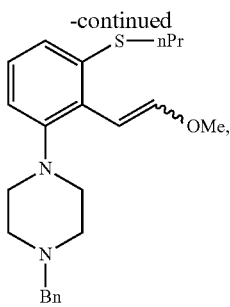

or a salt or solvate thereof.

In another aspect, the invention is directed to a compound of formula (IV), or a salt or solvate thereof

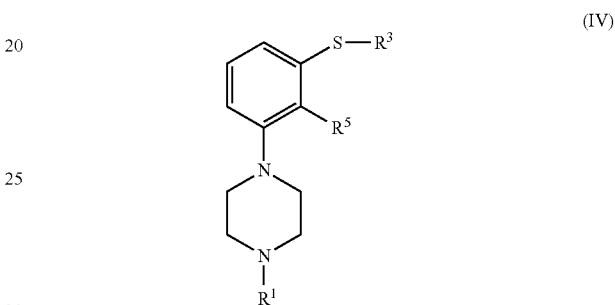

(IV)

wherein
R$^1$ is selected from hydrogen, an amino protecting group, —(CH$_2$)$_n$—X, —(CH$_2$)$_n$—OR,

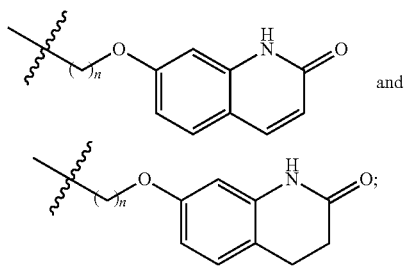

and n is an integer from 1 to 6;
X is a leaving group;
R is selected from H and a hydroxyl protecting group;
R$^3$ is selected from C$_1$-C$_6$ alkyl, C$_6$-C$_{10}$ aryl, (C$_6$-C$_{10}$)aryl(C$_1$-C$_6$)alkyl, —C(O)OR", —C(S)OR" and —C(O)R";
R" is selected from C$_1$-C$_6$ alkyl, C$_6$-C$_{10}$ aryl and (C$_6$-C$_{10}$)aryl(C$_1$-C$_6$)alkyl;
R$^5$ is selected from —CHO, —CN, —C(O)OR'" and —C(O)X";
X" is halogen; and
R'" is selected from H, C$_1$-C$_6$ alkyl, C$_6$-C$_{10}$ aryl and (C$_6$-C$_{10}$)aryl(C$_1$-C$_6$)alkyl,
with the proviso that when R$^1$ is hydrogen and R$^3$ is methyl, then R$^5$ is not —CN.

Preferred embodiments for R$^1$, R$^3$, R$^5$, n, X, X", R, R', R" and R'" are as defined above. In a particular embodiment, the compound of formula (IV) is a compound of formula (IVa), or a salt or solvate thereof

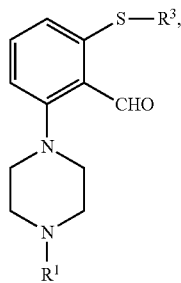

(IVa)

wherein $R^1$ is selected from hydrogen, an amino protecting group, $-(CH_2)_4-X$, $-(CH_2)_4-OR$,

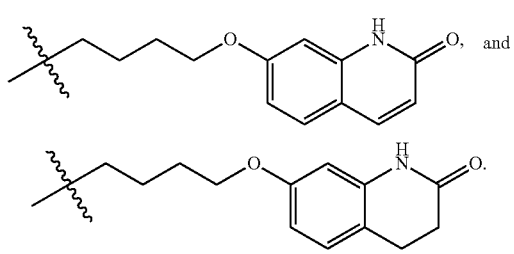

X is a leaving group;

R is selected from H and a hydroxyl protecting group;

$R^3$ is selected from $C_1$-$C_6$ alkyl, $C_6$-$C_{10}$ aryl, $(C_6$-$C_{10})$aryl $(C_1$-$C_6)$alkyl, $-C(O)OR''$, $-C(S)OR''$ and $-C(O)R''$;

$R''$ is selected from $C_1$-$C_6$ alkyl, $C_6$-$C_{10}$ aryl and $(C_6$-$C_{10})$aryl$(C_1$-$C_6)$alkyl.

In a preferred embodiment, the compound of formula (IV) is selected from

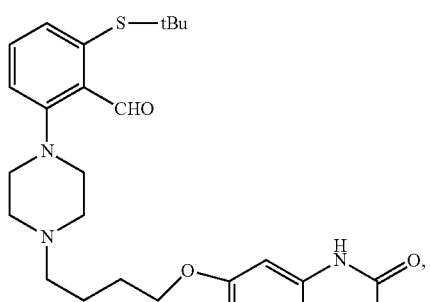

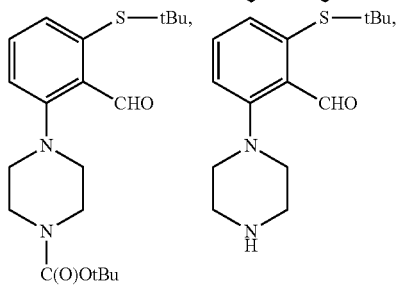

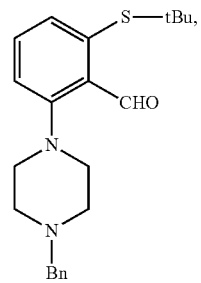

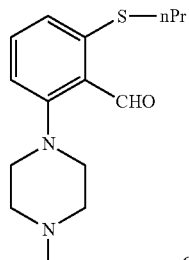

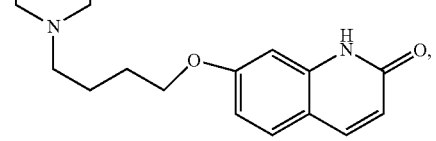

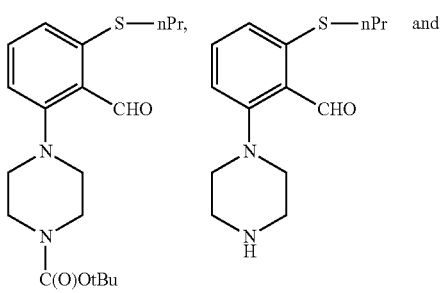

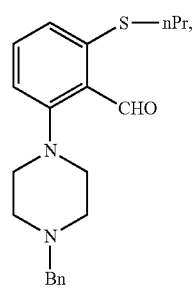

or a salt or solvate thereof.

The following examples illustrate the invention and should not be considered as limitative of the invention.

EXAMPLES

1.—Synthesis of N-Boc-piperazine 1

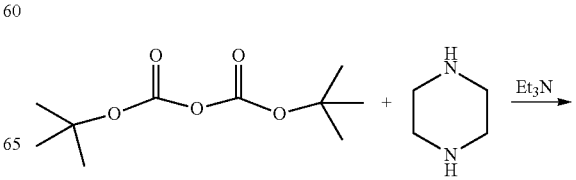

-continued

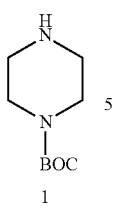

Piperazine (20 g, 232.5 mmol) was dissolved in MeOH (20 ml) and Et₃N (48.5 ml, 348.8 mmol) was added. A solution of Boc anhydride (20.27 g, 92.87 mmol) in MeOH (40 ml+10 ml for washing) was dropwise added. The mixture was stirred overnight at room temperature. The solvent was evaporated, the product was extracted with ethyl acetate and the solid was washed with ethyl acetate. 50 ml of a concentrated solution of bicarbonate were added to the organic phase to remove the excess of piperazine. The organic phase was washed with bicarbonate two more times. The aqueous phase was extracted with 40 ml of ethyl acetate. The organic phases were combined, dried over MgSO4, filtered and evaporated to dryness. A beige/white solid was obtained (14.58 g, 84%).

2.—Synthesis of Compound 2

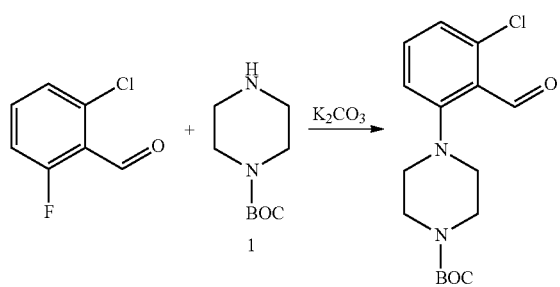

A mixture of Boc-piperazine 1 (14.58 g, 78.28 mmol), K₂CO₃ (10.82 g, 78.28 mmol) and 2-chloro-6-fluoro-benzaldehyde (8.30 g, 52.34 mmol) in DMF (27 ml), was heated at 90-100° C. overnight. When the reaction was complete, the crude reaction was poured over 500 ml of water and stirred for 30 min. The initially formed oil solidified and was filtered and the precipitate was washed with water. A mass of 18.19 g was obtained. 1.026 g of the crude product were purified by chromatography to yield 0.97 g of the pure product together with di-Boc-piperazine (87% yield).

¹H-NMR (400 MHz, CDCl₃): δ (ppm) 10.37 (s, 1H), 7.38 (d, J=8.1 Hz, 1H), 7.12 (dd, J=8.1, 0.9 Hz, 1H), 7.04-6.95 (m, 1H), 3.70-3.55 (m, 4H), 3.02 (s, 4H), 1.48 (s, 9H). ¹³C-NMR (101 MHz, CDCl₃): δ (ppm) 189.16, 155.48, 154.61, 137.23, 134.09, 125.87, 124.60, 117.72, 79.90, 53.25, 43.56, 28.33 (d, J=2.7 Hz).

3.—Synthesis of Compound 3

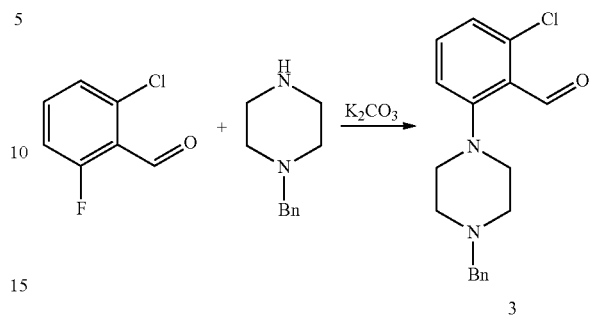

A mixture of 1-benzyl-piperazine (5.66 g, 32.16 mmol), K₂CO₃ (4.81 g, 34.84 mmol) and 2-chloro-6-fluoro-benzaldehyde (4.25 g, 26.80 mmol) in DMF (25 ml), was heated at 90-100° C. overnight. When the reaction was complete, the crude reaction was poured over 150 ml of water and stirred for 30 min. The solid was filtered and the precipitate was washed with water. The solid was dissolved again with Ethyl acetate, dried over MgSO₄, filtered and evaporated. The crude product was purified by chromatography (Ethyl acetate:Heptane 1/5) to yield 7.68 g of the pure product 3 (91% yield).

¹H-NMR (400 MHz, CDCl₃): δ (ppm) 10.29 (s, 1H), 7.43-7.24 (m, 6H), 7.06 (d, J=7.9 Hz, 1H), 6.99 (d, J=8.3 Hz, 1H), 3.57 (s, 2H), 3.27-2.97 (m, 4H), 2.63 (s, 4H). ¹³C-NMR (101 MHz, CDCl₃): δ (ppm) 189.65, 189.63, 156.20, 137.86, 133.98, 129.20, 128.29, 127.19, 124.30, 117.53, 62.97, 53.57, 53.01.

4.—Synthesis of Compound 4

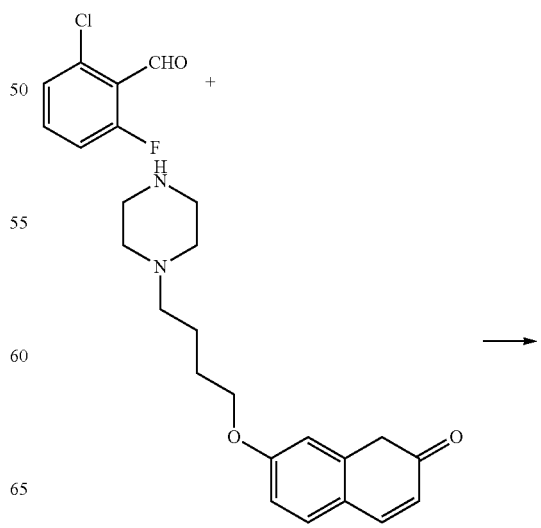

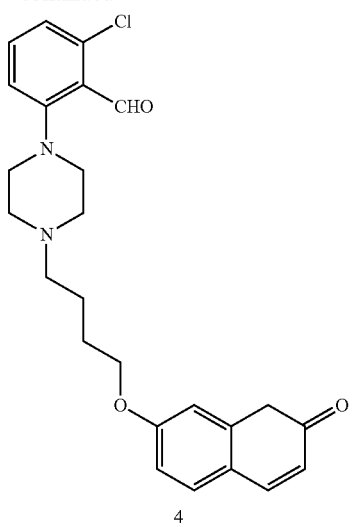

4

A mixture of 1-quinolone-piperazine (0.2 g, 0.66 mmol), K$_2$CO$_3$ (0.14 g, 0.99 mmol) and 2-chloro-6-fluoro-benzaldehyde (0.14 g, 0.86 mmol) in DMF (5 ml), was heated at 90-100° C. overnight. When the reaction was complete, the crude reaction was poured over 50 ml of water and was extracted with Ethyl Acetate (2×10 ml). The organic phase was dried over MgSO$_4$, filtered and evaporated. The crude product was purified by chromatography to yield 0.26 g of the pure product 4 (89% yield).

$^1$H-NMR (400 MHz, CDCl$_3$): δ (ppm) 10.95 (s, 1H), 10.30 (d, J=1.1 Hz, 1H), 7.69 (d, J=9.5 Hz, 1H), 7.43 (dd, J=8.7, 1.1 Hz, 1H), 7.35 (d, J=1.1 Hz, 1H), 7.07 (s, 1H), 6.99 (d, J=8.2 Hz, 1H), 6.84-6.74 (m, 1H), 6.70 (d, J=2.3 Hz, 1H), 6.50 (dd, J=9.4, 1.1 Hz, 1H), 4.11-4.03 (m, 2H), 3.09 (t, J=4.8 Hz, 4H), 2.66 (s, 4H), 2.50 (s, 2H), 1.87 (s, 2H), 1.72 (s, 2H). $^{13}$C-NMR (101 MHz, CDCl$_3$): δ (ppm) 189.46, 165.13, 161.28, 155.96, 140.80, 140.37, 136.16, 133.96, 128.89, 125.64, 124.22, 117.63, 117.46, 114.07, 112.66, 98.89, 67.95, 57.90, 53.35, 52.94, 27.04, 23.15.

5.—Synthesis of Compound 5

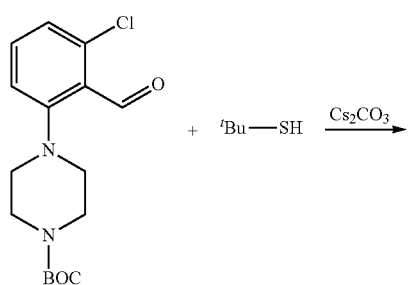

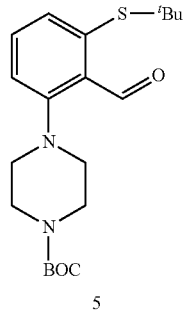

5

17.16 g of crude compound 2 and the 0.97 g obtained after column chromatography were combined. This corresponds to 15.31 g (47.15 mmol) of pure compound 2. It was dissolved in DMF (40 ml) and t-butylthiol (12 ml, 106.50 mmol) and Cs$_2$CO$_3$ (34.70 g, 106.50 mmol) were added. The temperature was raised to 90-100° C. and the reaction mixture stirred for 1 hour and 45 min. When the reaction was complete, the reaction crude was poured over 500 ml of water and stirred for 30 min. An oil, less dense than water, was obtained. It was filtered through earth and washed with water. The oil was dissolved in acetone and evaporated to dryness. On allowing to stand the oil for the weekend, a solid was obtained. It was washed with water until water did not get yellow any more. 1.01 g of the crude product were purified by chromatography to yield 0.97 g of the pure product together with di-Boc-piperazine. Taking this into account, the yield was almost quantitative. We got 20.70 g of crude product, of which 17.83 g are pure compound.

$^{13}$C NMR (126 MHz, CDCl$_3$) δ 192.15, 154.71, 153.52, 138.76, 132.95, 132.56, 132.48 (d, J=5.0 Hz), 119.67, 79.63, 53.12, 47.68, 43.71 (d, J=109.3 Hz), 31.10, 28.35 (d, J=6.4 Hz). $^1$H NMR (400 MHz, CDCl$_3$) δ 10.64 (s, 1H), 7.42 (d, J=8.0 Hz, 1H), 7.29 (dd, J=7.7, 1.1 Hz, 1H), 7.07 (d, J=8.2 Hz, 1H), 3.64 (t, J=5.0 Hz, 4H), 3.01 (t, J=4.9 Hz, 4H), 1.48 (s, 9H), 1.29 (s, 9H).

6.—Synthesis of Compound 6

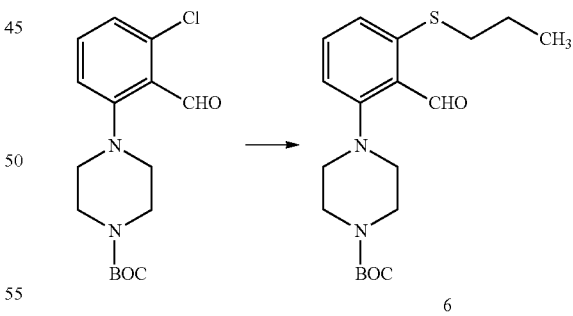

6

1.0 g (3.28 mmol) of pure compound 2 was dissolved in DMF (4.0 ml) and propanethiol (0.59 ml, 6.56 mmol) and Cs$_2$CO$_3$ (2.14 g, 6.56 mmol) were added. The temperature was raised to 90-100° C. and the reaction mixture stirred for 1.5 hours. When the reaction was complete, the reaction crude was poured over 250 ml of water and stirred for 30 min. The solid was filtered through earth and washed with water. The solid was dissolved in dichloromethane, dried over MgSO$_4$, filtered and evaporated to yield product 6 (85% yield).

¹H-NMR (500 MHz, CDCl₃): δ (ppm) 10.42 (d, J=0.6 Hz, 1H), 7.41 (s, 1H), 7.04 (d, J=8.1 Hz, 1H), 6.85 (dd, J=8.1, 0.9 Hz, 1H), 3.60 (t, J=5.0 Hz, 5H), 3.00 (s, 4H), 2.95-2.85 (m, 2H), 1.76 (d, J=7.3 Hz, 1H), 1.48 (s, 11H), 1.08 (s, 2H).

7.—Synthesis of Compound 7

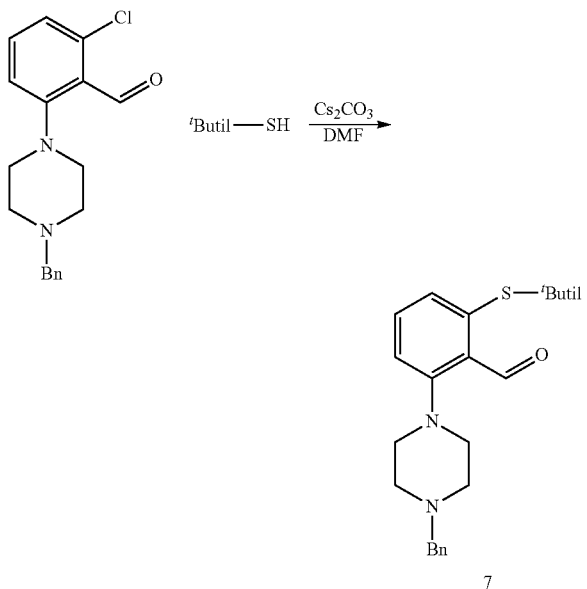

The intermediate compound 3 (3.0 g 9.53 mmol) was dissolved in DMF (10 ml) and t-butylthiol (4.30 ml, 38.12 mmol) and Cs₂CO₃ (12.42 g, 38.12 mmol) were added. The temperature was raised to 90-100° C. and the reaction mixture stirred for 3 hours. When the reaction was complete, the reaction crude was poured over 200 ml. An oil, less dense than water, was obtained. It was filtered through earth and washed with water. The oil was dissolved in Ethyl Acetate, was dried over MgSO₄, filtered and evaporated to yield 3.34 g of crude product 7 (95% yield).

¹H-NMR (400 MHz, CDCl₃): δ (ppm) 10.59 (d, J=0.6 Hz, 1H), 7.34 (d, J=0.7 Hz, 7H), 7.09 (dt, J=8.2, 0.8 Hz, 1H), 3.59 (s, 2H), 3.17-3.04 (m, 4H), 2.68 (d, J=4.9 Hz, 4H), 1.30 (s, 9H). ¹³C-NMR (101 MHz, CDCl₃): δ (ppm) 192.38, 154.09, 138.38, 138.03, 132.81, 131.82, 129.25, 128.22, 127.08, 119.34, 63.06, 53.25, 53.14, 47.61, 31.15

8.—Synthesis of Compound 8

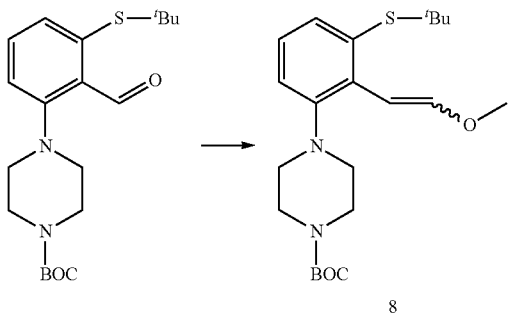 [SMILES: CC(C)(C)OC(=O)N1CCN(c2cccc(SC(C)(C)C)c2C=O)CC1 ; COC=Cc1c(SC(C)(C)C)cccc1N1CCN(C(=O)OC(C)(C)C)CC1]

A flask was charged with well dried potassium tert-butoxide (17.52 g, 156.11 mmol) and (PPh₃CH₂OMe)Cl (58.87 g, 171.72 mmol) under inert atmosphere. The flask was placed in an ice bath and dry THF (80 ml) was added. It was stirred for 30 min. Then, 19.96 g of crude compound 5 (16.96 g of pure compound, 44.81 mmol) were added and the mixture was stirred overnight. When the reaction was complete, NH₄Cl was added and the mixture extracted with the THF of the reaction and ethyl acetate. The organic phase was washed three times with a saturated aqueous solution of NH₄Cl (50 ml), the aqueous phases were combined and extracted with ethyl acetate (40 ml). The organic phases were combined, dried, filtered and evaporated. A dark color oil was obtained. The compound was extracted with a mixture of acetate/heptane 1/10 (100 ml) under stirring. A dark brown solid precipitated, which was washed with heptane. The solvent was evaporated to yield a brown oil. The compound was extracted with heptane under stirring overnight, and a beige solid precipitated. It was filtered and washed with heptane. The solvent was evaporated to yield an oily crude (31 g).

E Isomer
¹³C NMR (101 MHz, CDCl₃) δ 154.71, 152.43, 150.85, 135.90, 134.75, 132.34, 125.20, 119.94, 102.04, 79.48, 55.77, 51.34, 47.65, 43.95, 31.13, 28.34.

E/Z Mixture
¹³C NMR (101 MHz, CDCl₃) δ 154.80 (t, J=2.5 Hz), 152.44 (d, J=2.3 Hz), 151.95 (d, J=2.1 Hz), 150.88 (d, J=2.2 Hz), 146.44 (d, J=2.2 Hz), 135.93 (t, J=2.6 Hz), 134.76 (d, J=2.2 Hz), 133.73 (d, J=2.2 Hz), 132.66 (d, J=2.2 Hz), 132.36 (d, J=1.9 Hz), 126.59 (d, J=2.1 Hz), 125.25 (d, J=2.3 Hz), 119.98 (d, J=2.2 Hz), 119.08 (d, J=2.2 Hz), 103.83 (d, J=2.2 Hz), 102.09 (d, J=2.0 Hz), 79.58 (d, J=1.8 Hz), 79.44 (d, J=1.7 Hz), 59.18 (d, J=2.1 Hz), 55.88 (d, J=2.0 Hz), 51.55, 51.36, 47.75 (d, J=1.9 Hz), 46.72 (d, J=1.9 Hz), 44.11, 31.19 (dd, J=4.6, 2.3 Hz), 28.40 (d, J=2.3 Hz). ¹H NMR (400 MHz, CDCl₃) δ 7.67 (d, J=12.9 Hz, 1H), 7.32 (d, J=1.4 Hz, 2H), 7.14 (s, 1H), 7.09-6.89 (m, 3H), 6.36 (d, J=13.0 Hz, 1H), 6.03 (d, J=6.8 Hz, 1H), 5.48 (d, J=6.7 Hz, 1H), 3.72 (s, 4H), 3.64 (s, 2H), 3.53 (s, 7H), 2.90 (s, 7H), 1.48 (s, 16H), 1.27 (d, J=2.5 Hz, 17H).

9.—Synthesis of Compound 9

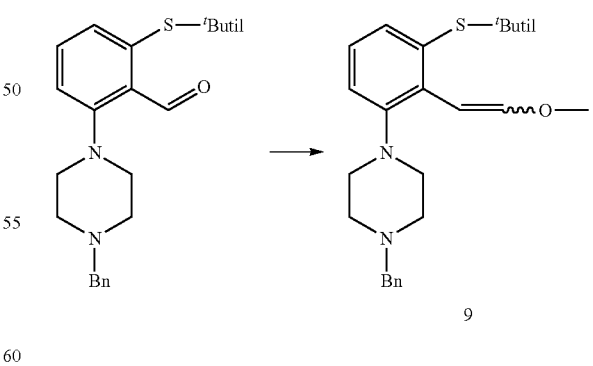

A flask was charged with well dried potassium tert-butoxide (3.21 g, 28.59 mmol) and (PPh₃CH₂OMe)Cl (10.78 g, 31.45 mmol) under inert atmosphere. The flask was placed in an ice bath and dry THF (25 ml) was added. It was stirred for 30 min. Then, the crude compound 7 (2.93 g, 7.95 mmol) was added and the mixture was stirred overnight. When the reaction was complete, NH₄Cl was added and the mixture extracted with Ethyl acetate. The organic phase was dried over MgSO$_4$, filtered and evaporated. The crude product was purified by chromatography (Ethyl acetate: Heptane 1/4) to yield 2.52 g of the pure product 9 (80% yield).

E/Z Mixture $^1$H NMR (400 MHz, CDCl$_3$) b 7.77 (d, J=13.0 Hz, 1H), 7.35 (s, 7H), 7.18-7.09 (m, 0H), 7.04 (d, J=0.9 Hz, 2H), 6.43 (d, J=12.9 Hz, 1H), 6.01 (d, J=6.7 Hz, 0H), 5.47 (d, J=6.8 Hz, 0H), 3.72 (s, 3H), 3.61 (s, 1H), 3.57 (s, 2H), 2.98 (d, J=5.0 Hz, 5H), 2.58 (s, 5H), 1.27 (d, J=4.3 Hz, 14H).

E Isomer $^1$H NMR (400 MHz, CDCl$_3$) b 7.76 (d, J=13.0 Hz, 1H), 7.34 (s, 6H), 7.04 (d, J=0.8 Hz, 2H), 6.42 (d, J=13.0 Hz, 1H), 3.71 (s, 3H), 3.56 (s, 2H), 2.98 (s, 4H), 2.58 (s, 4H), 1.27 (s, 9H). $^{13}$C NMR (126 MHz, Chloroform-d) b 152.45, 151.25, 138.12, 135.85, 134.57, 132.20, 129.24, 128.26, 127.11, 125.23, 120.13, 102.59, 63.24, 56.04, 53.60, 51.44, 47.82, 31.27.

10.—Synthesis of Compound 10

The crude compound 9 (0.15 g of pure compound, 0.39 mmol) was dissolved in CH$_2$Cl$_2$ (2 ml) and was placed in an ice bath. A flask was charged with a 1:1 mixture of trifluoroacetic acid and triflic acid (0.4 ml+0.4 ml) under inert atmosphere was placed in an ice bath. The acid mixture was slowly added over the compound 9. The mixture was stirred for 1 hour. The mixture was basified by addition of a solution of 20% NaOH. The compound was extracted with ethyl acetate, dried over MgSO$_4$, filtered and evaporated.

$^1$H NMR (400 MHz, CDCl$_3$) δ 7.54 (s, 1H), 7.44-7.26 (m, 8H), 6.90 (dd, J=7.7, 0.8 Hz, 1H), 3.64 (s, 2H), 3.20 (s, 4H), 2.72 (s, 4H). $^{13}$C NMR (126 MHz, Chloroform-d) δ 148.58, 141.11, 138.11, 134.11, 129.28, 128.30, 127.15, 125.03, 124.88, 121.96, 116.93, 112.19, 63.20, 53.52, 52.16.

12.—Synthesis of Compound 12

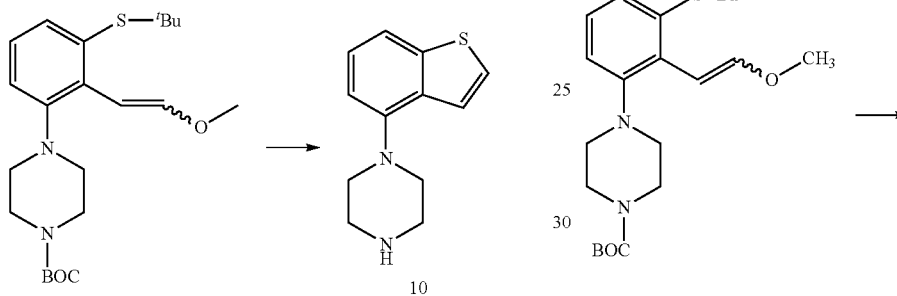

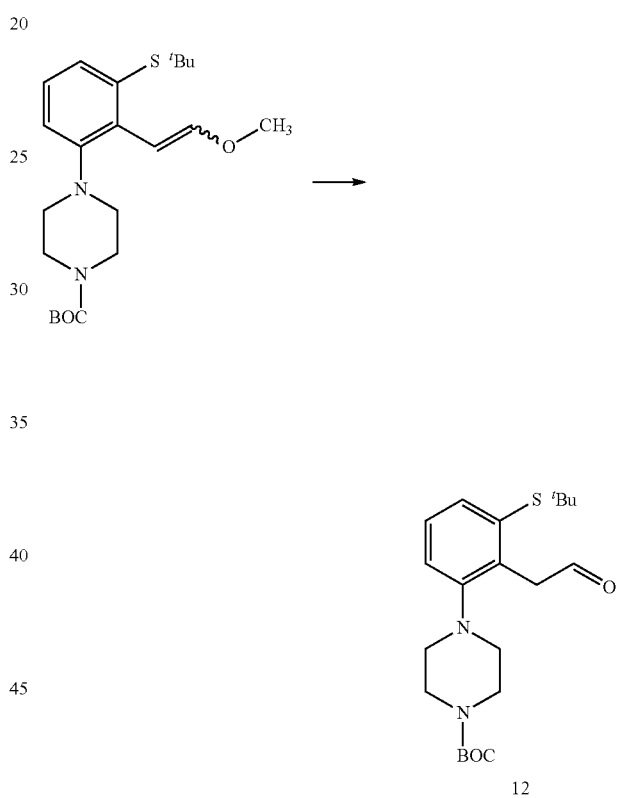

7.37 g of the crude compound 8 (4.30 g of pure compound, 10.60 mmol) were dissolved in CH$_2$Cl$_2$ (20 ml). Concentrated hydrochloric acid (9 ml) was added and the mixture was stirred under reflux for 1 h. CH$_2$Cl$_2$ (20 ml) and HCl 2N (20 ml) were added. The aqueous phase was washed four times with CH$_2$Cl$_2$ to remove the residues of triphenyl phosphine oxide and triphenyl phosphine. The aqueous phase was basified by addition of NaOH. The compound was extracted with ethyl acetate, dried over MgSO$_4$, filtered and evaporated. A red oil was obtained (2.03 g). $^{13}$C NMR (101 MHz, CDCl$_3$) δ 148.93, 141.11, 134.12, 124.96 (d, J=9.9 Hz), 121.90, 116.96, 112.18, 53.55, 46.44. $^1$H NMR (400 MHz, CDCl$_3$) δ 7.60-7.50 (m, 1H), 7.42 (d, J=0.8 Hz, 1H), 7.39 (s, 1H), 7.28 (s, 1H), 6.90 (d, J=0.8 Hz, 1H), 3.12 (s, 8H).

11.—Synthesis of Compound 11

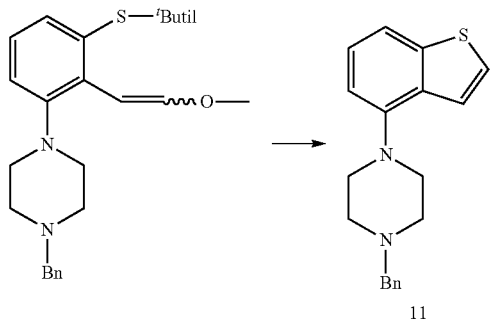

0.1279 g of the crude compound 8 (0.314 mmol) were dissolved in CH$_2$CO$_2$ (0.6 ml). Formic acid (0.3 ml) was added and the mixture was stirred at room temperature overnight. The mixture was basified by addition of a concentrated solution of bicarbonate (10 ml). The aqueous phase was washed with CH$_2$Cl$_2$ (5 ml). The organic phases were combined, dried over MgSO$_4$, filtered and evaporated. The crude product was purified by chromatography (Ethyl acetate:Heptane 1/3) to yield 0.062 g of the pure product 12 (48% yield).

$^{13}$C NMR (101 MHz, CDCl$_3$) δ 199.04, 151.86, 137.17, 135.74, 134.45, 127.83, 122.10, 79.76, 52.07, 47.73, 44.93, 43.44, 30.94, 28.39. $^1$H NMR (400 MHz, CDCl$_3$) δ 9.45 (s, 1H), 7.47 (d, J=1.2 Hz, 1H), 7.28 (s, 1H), 7.20 (dd, J=8.0, 1.2 Hz, 1H), 4.10 (d, J=2.2 Hz, 2H), 2.81 (s, 8H), 1.47 (s, 9H), 1.27 (s, 9H).

13.—Synthesis of Compound 13

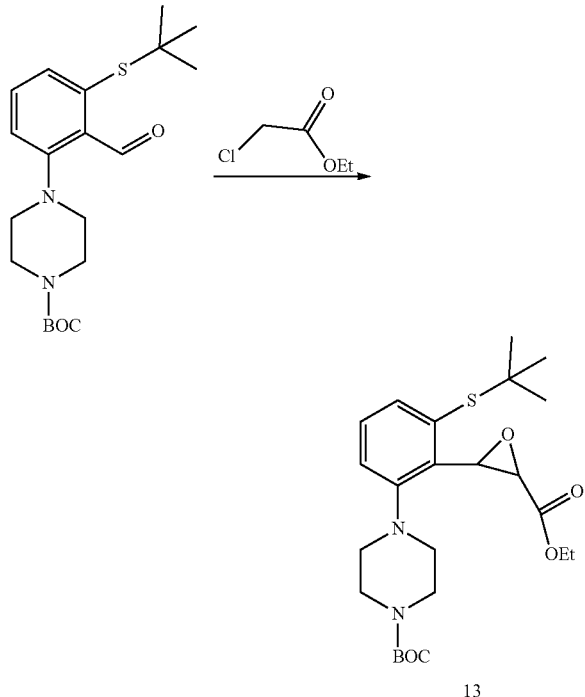

A flask was charged with intermediate 5 (2.216 g, 5.616 mmol) and dissolved in CH$_2$Cl$_2$ (15 ml) under inert atmosphere. The flask was placed in an ice bath and dry Ethyl chloroacetate (0.72 ml, 6.74 mmol, 1.2 equivalents) was added. Then, t-BuOK (0.945 g, 8.42 mmol, 1.5 equivalents) was added slowly and the mixture was stirred at room temperature overnight. When the reaction was complete, a saturated solution of NaCl in water (20 ml) was added and the mixture extracted with ethyl acetate (15 ml). The crude product was purified by column chromatography.

$^1$H-NMR (400 MHz, CDCl$_3$): δ (ppm) δ 7.32 (s, 1H), 7.26 (s, 1H), 7.07 (d, J=7.9 Hz, 1H), 4.40 (d, J=1.9 Hz, 1H), 3.84-3.79 (m, 1H), 3.58 (t, J=5.2 Hz, 4H), 2.89 (s, 4H), 1.47 (s, 9H), 1.30 (s, 9H). $^{13}$C NMR (101 MHz, CDCl3) δ 7.32 (s, 1H), 7.26 (s, 1H), 7.07 (d, J=7.9 Hz, 1H), 4.40 (d, J=1.9 Hz, 1H), 3.84-3.79 (m, 1H), 3.58 (t, J=5.2 Hz, 4H), 2.89 (s, 4H), 1.47 (s, 9H), 1.30 (s, 9H).

14.—Synthesis of Compound 14

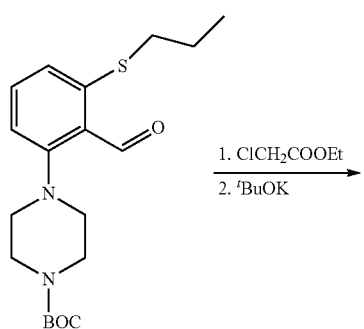

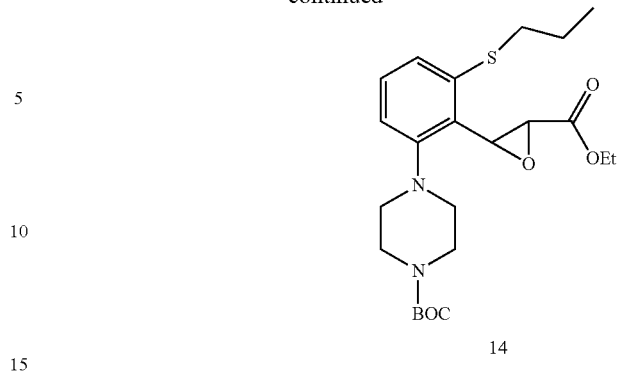

A flask was charged with intermediate 6 (1.01 g, 2.75 mmol) and dissolved in CH$_2$Cl$_2$ (5 ml) under inert atmosphere. The flask was placed in an ice bath and dry Ethyl chloroacetate (0.46 ml, 2.0 equivalents) was added. Then, t-BuOK (0.61 g, 2.0 equivalents) was added slowly and the mixture was stirred at room temperature for 2 hours. When the reaction was complete, a saturated solution of NaCl in water (10 ml) was added and the mixture was extracted with ethyl acetate (10 ml), the organic phase was dried over MgSO$_4$, filtered and evaporated to obtain the product 14 (85%).

$^1$H-NMR (500 MHz, CDCl$_3$): δ (ppm) δ 7.23 (d, J=7.9 Hz, 1H), 7.05 (dd, J=8.0, 0.9 Hz, 1H), 6.85 (dd, J=8.1, 0.9 Hz, 1H), 4.31 (d, J=7.1 Hz, 2H), 4.20 (d, J=2.1 Hz, 1H), 3.71 (dd, J=2.2, 0.5 Hz, 1H), 3.55 (s, 5H), 2.92 (s, 1H), 2.85 (d, J=24.7 Hz, 1H), 1.71 (d, J=7.3 Hz, 2H), 1.47 (s, 13H), 1.33 (d, J=0.5 Hz, 2H), 1.04 (s, 2H).

15.—Synthesis of Compound 10

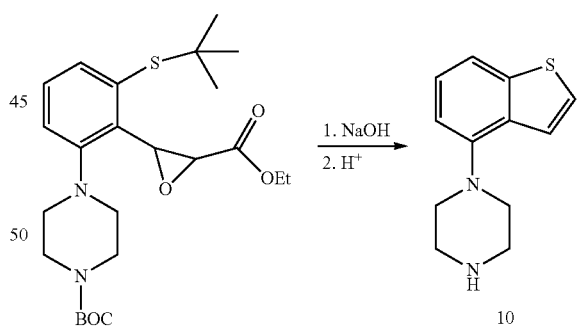

2.0 g of the crude compound 13 (1.20 g of pure compound, 2.98 mmol) were dissolved in a mixture of CH$_2$Cl$_2$ and MeOH 1/1 (10 ml). A solution of NaOH 1M (10.0 ml) was added and the mixture was stirred at room temperature for 3 h. The mixture was evaporated, then was acidified by addition of a concentrated solution of HCl (3 ml) and stirred under reflux for 30 minutes. The mixture was neutralized by addition of an aqueous solution of NaOH 20% and the mixture extracted with ethyl acetate (10 ml). The organic phase was dried over MgSO$_4$, filtered and evaporated. Compound 10 was obtained (65% yield).

The invention claimed is:

1. A process for preparing a compound of formula (I), or a salt or solvate thereof

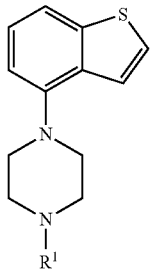
(I)

wherein
R¹ is selected from the group consisting of hydrogen, an amino protecting group, —(CH$_2$)$_n$—X, —(CH$_2$)$_n$—OR,

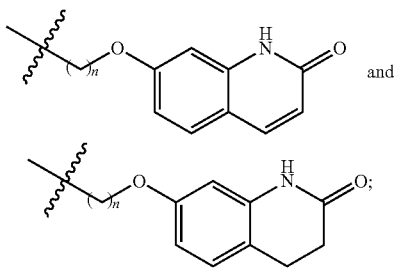
and n is an integer from 1 to 6;
X is a leaving group;
R is selected from the group consisting of H and a hydroxyl protecting group;
which process comprises cyclization of a compound of formula (II), or a salt or solvate thereof

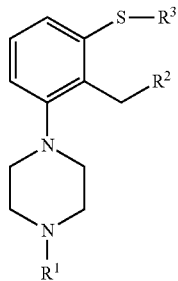
(II)

wherein
R¹ is as defined above;
R² is selected from the group consisting of —CHO, —CN, —C(O)OR' and —C(O)X';
X' is halogen;
R' is selected from the group consisting of H, C$_1$-C$_6$ alkyl, C$_6$-C$_{10}$ aryl and (C$_6$-C$_{10}$)aryl(C$_1$-C$_6$)alkyl;
R³ is selected from the group consisting of C$_1$-C$_6$ alkyl, C$_6$-C$_{10}$ aryl, (C$_6$-C$_{10}$)aryl(C$_1$-C$_6$)alkyl, —C(O)OR", —C(S)OR" and —C(O)R"; and
R" is selected from the group consisting of C$_1$-C$_6$ alkyl, C$_6$-C$_{10}$ aryl and (C$_6$-C$_{10}$)aryl(C$_1$-C$_6$)alkyl.

2. A process for preparing a compound of formula (I), or a salt or solvate thereof

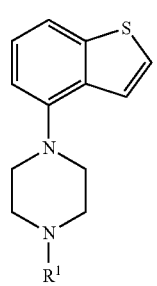
(I)

wherein
R¹ is selected from the group consisting of hydrogen, an amino protecting group, —(CH$_2$)$_n$—X, —(CH$_2$)$_n$—OR,

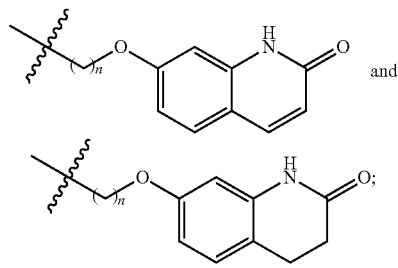
and n is an integer from 1 to 6;
X is a leaving group;
R is selected from the group consisting of H and a hydroxyl protecting group;
which process comprises cyclization of a compound of formula (III), or a salt or solvate thereof

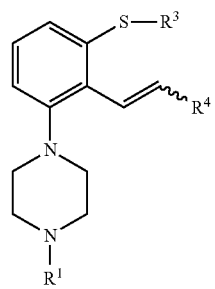
(III)

wherein
R¹ is as defined above;
R' is selected from the group consisting of halogen and —OR';
R' is selected from the group consisting of C$_1$-C$_6$ alkyl, C$_6$-C$_{10}$ aryl and (C$_6$-C$_{10}$)aryl(C$_1$-C$_6$)alkyl;
R³ is selected from the group consisting of C$_1$-C$_6$ alkyl, C$_6$-C$_0$ aryl, (C$_6$-C$_{10}$)aryl(C$_1$-C$_6$)alkyl, —C(O)OR", —C(S)OR" and —C(O)R"; and
R" is selected from the group consisting of C$_1$-C$_6$ alkyl, C$_6$-C$_{10}$ aryl and (C$_6$-C$_{10}$)aryl(C$_1$-C$_6$)alkyl.

3. The process according to claim 1, which further comprises obtaining the compound of formula (II), or a salt or solvate thereof, by a process comprising homologation of a compound of formula (IV), or a salt or solvate thereof

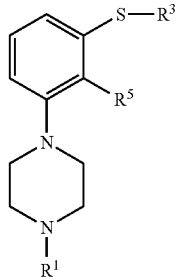
(IV)

wherein
R⁵ is selected from the group consisting of —CHO, —CN, —C(O)OR''' and —C(O)X'';
X'' is halogen; and
R''' is selected from the group consisting of H, $C_1$-$C_6$ alkyl, $C_6$-$C_{10}$ aryl and ($C_6$-$C_{10}$)aryl($C_1$-$C_6$)alkyl.

4. The process according to claim 2, which further comprises obtaining the compound of formula (III), or a salt or solvate thereof, by a process comprising alkenylation of a compound of formula (V), or a salt or solvate thereof

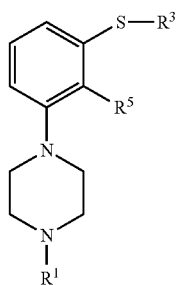
(IV)

wherein
R⁵ is —CHO.

5. The process according to claim 3, wherein R² and R⁵ are —CHO.

6. The process according to claim 5, wherein
R¹ is selected from the group consisting of hydrogen, an amino protecting group, —(CH₂)ₙ—X, —(CH₂)ₙ—OR,

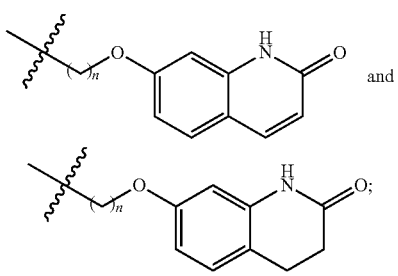

n is 4;
X is a leaving group;
R is selected from the group consisting of H and a hydroxyl protecting group;

R² is —CHO;
R³ is $C_1$-$C_6$ alkyl;
R⁴ is selected from the group consisting of halogen and —O$C_1$-$C_6$ alkyl;
R⁵ is —CHO.

7. The process according to claim 1, wherein the cyclization of a compound of formula (II), or a salt or solvate thereof, is carried out in the presence of an acid.

8. The process according to claim 1, which further comprises converting a compound of formula (I), or a salt or solvate thereof, wherein R' is selected from the group consisting of hydrogen, an amino protecting group, —(CH₂)₄—X and —(CH₂)₄—OR; X is a leaving group; and R is selected from the group consisting of H and a hydroxyl protecting group; into a compound of formula (I), or a salt or solvate thereof, wherein R¹ is selected from the group consisting of

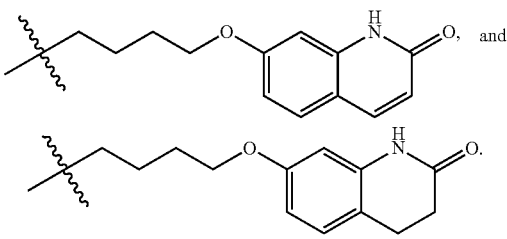

9. The process according to claim 1, wherein the compound of formula (I) is (1-benzothiophen-4-yl)piperazine or Brexpiprazole, or a salt or solvate thereof.

10. The process according to claim 1 for preparing Brexpiprazole which comprises cyclization in the presence of an acid of a compound of formula (IIa), or a salt or solvate thereof

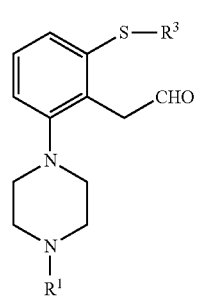
(IIa)

wherein
R¹ is selected from the group consisting of hydrogen, an amino protecting group, —(CH₂)₄—X, —(CH₂)₄—OR, and

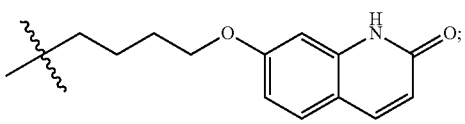 [SMILES: *CCCCOc1ccc2ccc(=O)[nH]c2c1]

X is a leaving group;
R is selected from the group consisting of H and a hydroxyl protecting group;
R³ is selected from the group consisting of $C_1$-$C_6$ alkyl, $C_6$-$C_{10}$ aryl, ($C_6$-$C_{10}$)aryl($C_1$-$C_6$)alkyl, —C(O)OR'', —C(S)OR'' and —C(O)R''; and R" is selected from the group consisting of $C_1$-$C_6$ alkyl, $C_6$-$C_{10}$ aryl and ($C_6$-$C_{10}$)aryl($C_1$-$C_6$)alkyl.

11. The process according to claim 2 for preparing Brexpiprazole which comprises cyclization in the presence of an acid of a compound of formula (IIIa), or a salt or solvate thereof

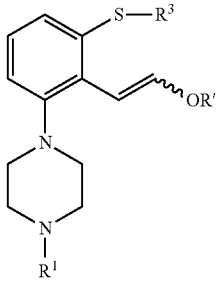
(IIIa)

wherein
$R^1$ is selected from the group consisting of hydrogen, an amino protecting group, —$(CH_2)_4$—X, —$(CH_2)_4$—OR, and

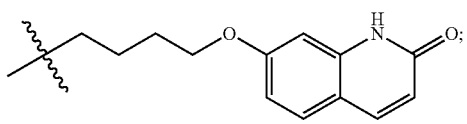 [SMILES: *CCCCOc1ccc2ccc(=O)[nH]c2c1]

X is a leaving group;
R is selected from the group consisting of H and a hydroxyl protecting group;

R' is selected from the group consisting of $C_1$-$C_6$ alkyl, $C_6$-$C_{10}$ aryl and ($C_6$-$C_{10}$)aryl($C_1$-$C_6$)alkyl;
$R^3$ is selected from the group consisting of $C_1$-$C_6$ alkyl, $C_6$-$C_{10}$ aryl, ($C_6$-$C_{10}$)aryl($C_1$-$C_6$)alkyl, —C(O)OR", —C(S)OR" and —C(O)R"; and
R" is selected from the group consisting of $C_1$-$C_6$ alkyl, $C_6$-$C_{10}$ aryl and ($C_6$-$C_{10}$)aryl($C_1$-$C_6$)alkyl.

12. The process according to claim 2, wherein the cyclization of a compound of formula (III), or a salt or solvate thereof, is carried out in the presence of an acid.

13. The process according to claim 2, which further comprises converting a compound of formula (I), or a salt or solvate thereof, wherein $R^1$ is selected from the group consisting of hydrogen, an amino protecting group, —$(CH_2)_4$—X and —$(CH_2)_4$—OR;
X is a leaving group; and
R is selected from the group consisting of H and a hydroxyl protecting group; into a compound of formula (I), or a salt or solvate thereof,
wherein $R^1$ is selected from the group consisting of

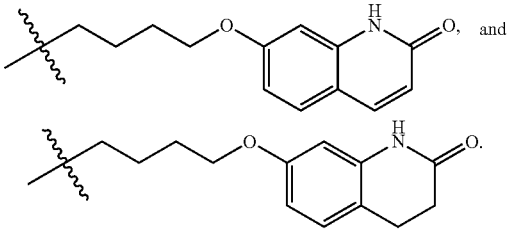

14. The process according to claim 2, wherein the compound of formula (I) is (1-benzothiophen-4-yl)piperazine or Brexpiprazole, or a salt or solvate thereof.

* * * * *